US010668140B2

(12) United States Patent
Sun et al.

(10) Patent No.: US 10,668,140 B2
(45) Date of Patent: Jun. 2, 2020

(54) NON-TOXIGENIC *CLOSTRIDIUM DIFFICILE* SPORES FOR USE IN ORAL VACCINATION

(71) Applicants: UNIVERSITY OF SOUTH FLORIDA, Tampa, FL (US); TRUSTEES OF TUFTS COLLEGE, Boston, MA (US)

(72) Inventors: Xingmin Sun, Tampa, FL (US); Abraham Sonenshein, Boston, MA (US)

(73) Assignees: University of South Floirida, Tampa, FL (US); Trustees of Tufts College, Boston, MA (US)

( * ) Notice: Subject to any disclaimer, the term of this patent is extended or adjusted under 35 U.S.C. 154(b) by 0 days.

(21) Appl. No.: 15/905,598

(22) Filed: Feb. 26, 2018

(65) Prior Publication Data
US 2018/0256697 A1   Sep. 13, 2018

Related U.S. Application Data

(60) Provisional application No. 62/463,497, filed on Feb. 24, 2017, provisional application No. 62/513,247, filed on May 31, 2017, provisional application No. 62/588,777, filed on Nov. 20, 2017.

(51) Int. Cl.
*A61K 39/00* (2006.01)
*A61K 39/08* (2006.01)
*C12N 9/10* (2006.01)
*C12N 9/52* (2006.01)
*C07K 14/33* (2006.01)

(52) U.S. Cl.
CPC .............. *A61K 39/08* (2013.01); *C07K 14/33* (2013.01); *C12N 9/1048* (2013.01); *C12N 9/52* (2013.01); *A61K 2039/542* (2013.01); *A61K 2039/575* (2013.01); *C07K 2319/40* (2013.01)

(58) Field of Classification Search
None
See application file for complete search history.

(56) References Cited

U.S. PATENT DOCUMENTS

| 2015/0044250 A1 | 2/2015 | Heinrichs et al. |
| 2015/0132333 A1 | 5/2015 | Scarselli et al. |
| 2016/0074496 A1 | 3/2016 | Lanis et al. |
| 2016/0326222 A1 | 11/2016 | Logan et al. |

OTHER PUBLICATIONS

Babcock et al., "Human monoclonal antibodies directed against toxins A and B prevent Clostridium difficile-induced mortality in hamsters," Infect Immun (2006) 74(11): pp. 6339-6347.
Ghose et al., "Toll-like receptor 5-dependent immunogenicity and protective efficacy of a recombinant fusion protein vaccine containing the nontoxic domains of Clostridium difficile toxins A and B and *Salmonella enterica* serovar typhimurium flagellin in a mouse model of Clostridium difficile disease," Infect Immun (2013) 81(6): pp. 2190-2196.
Jarchum et al., "Toll-like receptor 5 stimulation protects mice from acute Clostridium difficile colitis," Infect Immun. (2011) 79(4): pp. 1498-1503.
Tian et al., "A novel fusion protein containing the receptor binding domains of C. difficile toxin A and toxin B elicits protective immunity against lethal toxin and spore challenge in preclinical efficacy models," Vaccine (2012) 30(28): pp. 4249-4258.
Wang et al., "A chimeric toxin vaccine protects against primary and recurrent Clostridium difficile infection," Infection and immunity 80.8 (2012): pp. 2678-2688.
Wang et al., "A chimeric protein comprising the glucosyltransferase and cysteine proteinase domains of toxin B and the receptor binding domain of toxin A induces protective immunity against Clostridium difficile infection in mice and hamsters," Hum Vaccin Immunotherapy (2015) 11(9): pp. 2215-2222.

*Primary Examiner* — Jennifer E Graser
(74) *Attorney, Agent, or Firm* — Meunier Carlin & Curfman LLC

(57) ABSTRACT

Described are non-toxigenic *Clostridium difficile* strains and spores. Also described are vaccines comprising the *Clostridium difficile* spores. Further described are methods of preventing or treating a *Clostridium difficile* infection in a subject in need thereof.

16 Claims, 20 Drawing Sheets

Specification includes a Sequence Listing.

B-G1 > B-CPD > B-RBD > A-RBD

FIG. 3

```
ATGAGTTTAGTTAATAGAAAACAGTTAGAAAAAATGGCAAATGTAAGATTTCGTACTCAAGAAGATG
AATATGTTGCAATATTGGATGCTTTAGAAGAATATCATAATATGTCAGAGAATACTGTAGTCGAAAA
ATATTTAAAATTAAAAGATATAAATAGTTTAACAGATATTTATATAGATACATATAAAAAATCTGGT
AGAAATAAAGCCTTAAAAAAATTTAAGGAATATCTAGTTACAGAAGTATTAGAGCTAAAGAATAAT
AATTTAACTCCAGTTGAGAAAAATTTACATTTTGTTGCGATTGGAGGTCAAATAAATGACACTGCTAT
TAATTATATAAATCAATGGAAAGATGTAAATAGTGATTATAATGTTAATGTTTTTTTATGATAGTAATG
CATTTTTGATAAACACATTGAAAAAAACTGTAGTAGAATCAGCAATAAATGATACACTTGAATCATT
TAGAGAAAACTTAAATGACCCTAGATTTGACTATAATAAATTCTTCAGAAAACGTATGGAAATAATT
TATGATAAACAGAAAAATTTCATAAACTACTATAAAGCTCAAAGAGAAGAAAATCCTGAACTTATAA
TTGATGATATTGTAAAGACATATCTTTCAAATGAGTATTCAAAGGAGATAGATGAACTTAATACCTAT
ATTGAAGAATCCTTAAATAAAATTACACAGAATAGTGGAAATGATGTTAGAAACTTTGAAGAATTTA
AAAATGGAGAGTCATTCAACTTATATGAACAAGAGTTGGTAGAAAGGTGGAATTTAGCTGCTGCTTC
TGACATATTAAGAATATCTGCATTAAAAGAAATTGGTGGTATGTATTTAGATGTTAATATGTTACCAG
GAATACAACCAGACTTATTTGAGTCTATAGAGAAACCTAGTTCAGTAACAGTGGATTTTGGGAAAT
GACAAAGTTAGAAGCTATAATGAAATACAAAGAATATATACCAGAATATACCTCAGAACATTTTGAC
ATGTTAGACGAAGAAGTTCAAAGTAGTTTTGAATCTGTTCTAGCTTCTAAGTCAGATAAATCAGAAA
TATTCTCATCACTTGGTGATATGGAGGCATCACCACTAGAAGTTAAAATTGCATTTAATAGTAAGGGT
ATTATAAATCAAGGGCTAATTTCTGTGAAAGACTCATATTGTAGCAATTTAATAGTAAAACAAATCG
AGAATAGATATAAAATATTGAATAATAGTTTAAATCCAGCTATTAGCGAGGATAATGATTTTAATAC
TACAACGAATACCTTTATTGATAGTATAATGGCTGAAGCTAATGCAGATAATGGTAGATTTATGATG
GAACTAGGAAAGTATTTAAGAGTTGGTTTCTTCCCAGATGTTAAAACTACTATTAAGTTAAGTGGCCC
TGAAGCATATGCGGCAGCTTATCAAGATTTATTAATGTTTAAAGAAGGCAGTATGAATATCCATTTG
ATAGAAGCTGATTTAAGAAACTTTGAAATCTCTAAAACTAATATTTCTCAATCAACTGAACAAGAAA
TGGCTAGCTTATGGTCATTTGACGATGCAAGAGCTAAAGCTCAATTTGAAGAATATAAAAGGAATTA
TTTTGAAGGTTCTCTTGGTGAAGATGATAATCTTGATTTTTCTCAAAATATAGTAGTTGACAAGGAGT
ATCTTTTAGAAAAAATATCTTCATTAGCAAGAAGTTCAGAGAGAGGATATATACACTATATTGTTCA
GTTACAAGGAGATAAAATTAGTTATGAAGCAGCATGTAACTTATTTGCAAAGACTCCTTATGATAGT
GTACTGTTTCAGAAAAATATAGAAGATTCAGAAATTGCATATTATTATAATCCTGGAGATGGTGAAA
TACAAGAAATAGACAAGTATAAAATTCCAAGTATAATTTCTGATAGACCTAAGATTAAATTAACATT
TATTGGTCATGGTAAAGATGAATTTAATACTGATATATTTGCAGGTTTTGATGTAGATTCATTATCCA
CAGAAATAGAAGCAGCAATAGATTTAGCTAAAGAGGATATTTCTCCTAAGTCAATAGAAATAAATTT
ATTAGGAGCTAATATGTTTAGCTACTCTATCAACGTAGAGGAGACTTATCCTGGAAAATTATTACTTA
AAGTTAAAGATAAAATATCAGAATTAATGCCATCTATAAGTCAAGACTCTATTATAGTAAGTGCAAA
TCAATATGAAGTTAGAATAAATAGTGAAGGAAGAAGAGAATTATTGGATCATTCTGGTGAATGGATA
AATAAAGAAGAAAGTGGTGGCTCTGGTATAACTGGATTTGTGACTGTAGGCGATGATAAATACTACT
TTAATCCAATTAATGGTGGAGCTGCTTCAATTGGAGAGACAATAATTGATGACAAAAATTATATTTC
AACCAAAGTGGAGTGTTACAAACAGGTGTATTTAGTACAGAAGATGGATTTAAATATTTTGCCCCAG
CTAATACACTTGATGAAAACCTAGAAGGAGAAGCAATTGATTTTACTGGAAAATTAATTATTGACGA
AAATATTTATTATTTTGATGATAATTATAGAGGAGCTGTAGAATGGAAAGAATTAGATGGTGAAATG
CACTATTTTAGCCCAGAAACAGGTAAAGCTTTTAAAGGTCTAAATCAAATAGGTGATTATAAATACT
ATTTCAATTCTGATGGAGTTATGCAAAAAGGATTTGTTAGTATAAATGATAATAAACACTATTTTGAT
GATTCTGGTGTTATGAAAGTAGGTTACACTGAAATAGATGGCAAGCATTTCTACTTTGCTGAAAACG
GAGAAATGCAAATAGGAGTATTTAATACAGAAGATGGATTTAAATATTTTGCTCATCATAATGAAGA
TTTAGGAAATGAAGAAGGTGAAGAAATCTCAGGTGGCTCTGGTAAAATGGTAACAGGAGTATTTAA
AGGACCTAATGGATTTGAGTATTTTGCACCTGCTAATACTCACAATAATAACATAGAAGGTCAGGCT
ATAGTTTACCAGAACAAATTCTTAACTTTGAATGGCAAAAAATATTATTTTGATAATGACTCAAAAG
CAGTTACTGGATGGCAAACCATTGATGGTAAAAAATATTACTTTAATCTTAACACTGCTGAAGCAGC
TACTGGATGGCAAACTATTGATGGTAAAAAATATTACTTTAATCTTAACACTGCTGAAGCAGCTACT
GGATGGCAAACTATTGATGGTAAAAAATATTACTTTAATACTAACACTTTCATAGCCTCAACTGGTTA
TACAAGTATTAATGGTAAACATTTTTATTTTAATACTGATGGTATTATGCAGATAGGAGTGTTTAAAG
GACCTAATGGATTTGAATACTTTGCACCTGCTAATACGGATGCTAACAACATAGAAGGTCAAGCTAT
ACTTTACCAAAATAAATTCTTAACTTTGAATGGTAAAAAATATTACTTTGGTAGTGACTCAAAAGCA
GTTACCGGACTGCGAACTATTGATGGTAAAAAATATTACTTTAATACTAACACTGCTGTTGCAGTTAC
TGGATGGCAAACTATTAATGGTAAAAAATACTACTTTAATACTAACACTTCTATAGCTTCAACTGGTT
ATACAATTATTAGTGGTAAACATTTTTATTTTAATACTGATGGTATTATGCAGATAGGAGTGTTTAAA
GGACCTGATGGATTTGAATACTTTGCACCTGCTAATACAGATGCTAACAATATAGAAGGTCAAGCTA
TACGTTATCAAAATAGATTCCTATATTTACATGACAATATATATTTTTGGTAATAATTCAAAAGCG
GCTACTGGTTGGGTAACTATTGATGGTAATAGATATTACTTCGAGCCTAATACAGCTATGGGTGCGA
ATGGTTATAAAACTATTGATAATAAAAATTTTTACTTTAGAAATGGTTTACCTCAGATAGGAGTGTTT
AAAGGGTCTAATGGATTTGAATACTTTGCACCTGCTAATACGGATGCTAACAATATAGAAGGTCAAG
CTATACGTTATCAAAATAGATTCCTACATTTACTTGGAAAAATATATTACTTTGGTAATAATTCAAAA
GCAGTTACTGGATGGCAAACTATTAATGGTAAAGTATATTACTTTATGCCTGATACTGCTATGGCTGC
AGCTGGTGGACTTTTCGAGATTGATGGTGTTATATATTTCTTTGGTGTTGATGGAGTAAAAGCCCCTG
GGATATATGGG (SEQ ID NO.: 2)
```

FIG. 18 aa sequence (1417 aa) for Tcd169

MSLVNRKQLEKMANVRFRTQEDEYVAILDALEEYHNMSENTVVEKYLKLKDINSLTDIYIDTYKKSGRNKALKKFKEYLVT
EVLELKNNNLTPVEKNLHFVAIGGQJNDTAINYINQWKDVNSDYNVNVFYDSNAFUNTLKKTVVESAINDTLESFRENL
NDPRFDYNKFFRKRMEIIYDKQKNFINYYKAQREENPELIDDIVKTYLSNEYSKEIDELNTYIEESLNKITQNSGNDVRNFE
EFKNGESFNLYEQELVERWNLAAASDILRISALKEIGGMYLDVNMLPGIQPDLFESIEKPSSVTVDFWEMTKLEAIMKYK
EYIPEYTSEHFDMLDEEVQSSFESVLASKSDKSEIFSSLGDMEASPLEVKIAFNSKGIINQSLISVKDSYCSNLIVKQIENRYK
ILNNSLNPAISEDNDFNTTTNTRDSIMAEANADNGRFMMELGKYLRVGFPDVKTTINLSGPEAYAAAYQDLLMFKEG
SMNIHLIEADLRNFEISKTNISQSTEQEMASLWSFDDARAKAQFEEYKRNYFEGSLGEDDNLDFSQNIVVDKEYLLEKISS
LARSSERGYIHYIVQLQGDKISYEAACNLFAKTPYDSVLFQKNIEDSEIAYYYNPGDGEIQEIDKYKIPSIISDRPKIKLTFIGH
GKDEFNTDIFAGFDVDSLSTEIEAAIDLAKEDISPKSIEINLLGANMFSYSINVEETYPGKLLLKVKDKISELMPSISQDSIVS
ANQYEVRINSEGRRELLDHSGEWINKEESGGSGITGFVTVGDDKYYFNPINGGAASIGETIIDDKNYYFNQSGVLQTGVF
STEDGFKYFAPANTLDENLEGEAIDFTGKLIIDENIYYFDDNYRGAVEWKELDGEMJHYFSPETGKAFKGLNQJGDYKYYF
NSDGVMQKGFVSINDNKHYFDDSGVMKVGYTEIDGKHFYFAENGEMQJGVFNTEDGFKYFAHHNEDLGNEEGEEIS
GGSGKMVTGVFKGPNGFEYFAPANTHNNNIEGQANVYQNKFLTLNGKKYYFDNDSKAVTGWQTIDGKKYYFNLNTAE
AATGWQTIDGKKYYFNLNTAEAATGWQTIDGKKYYFNTNTFIASTGYTSINGKHFYFNTDGIMQIGVFKGPNGFEYFAP
ANTDANNIEGQAILYQNKFLTLNGKKYYFGSDSKAVTGLRTIDGKKYYFNTNTAVAVTGWQTINGKKYYFNTNTSIAST
GYTIISGKHFYFNTDGIMQJGVFKGPDGFEYFAPANTDANNIEGQAIRYQNRFLYLHDNIYYFGNNSKAATGWVTIDGN
RYYFEPNTAMGANGYKTIDNKNFYFRNGLPQIGVFKGSNGFEYFAPANTDANNIEGQAIRYQNRFLHLLGKIYYFGNNS
KAVTGWQTINGKVYYFMPDTAMAAAGGLFEIDGVIYFFGVDGVKAPGIYG (SEQ ID NO.: 3)

FIG. 19 aa sequence (1210 aa) for mTcd138

```
MSLVNRKQLE KMANVRFRTQ EDEYVAILDA LEEYHNMSEN TVVEKYLKLK DINSLTDIYI DTYKKSGRNK
ALKKFKEYLV TEVLELKNNN LTPVEKNLHF VAIGGQINDT AINYINQWKD VNSDYNVNVF YDSNAFLINT
LKKTVVESAI NDTLESFREN LNDPRFDYNK FFRKRMEIIY DKQKNFINYY KAQREENPEL IIDDIVKTYL
SNEYSKEIDE LNTYIEESLN KITQNSGNDV RNFEEFKNGE SFNLYEQELV ERWNLAAASD ILRISALKEI
GGMYLDVNML PGIQPDLFES IEKPSSVTVD FWEMTKLEAI MKYKEYIPEY TSEHFDMLDE EVQSSFESVL
ASKSDKSEIF SSLGDMEASP LEVKIAFNSK GIINQGLISV KDSYCSNLIV KQIENRYKIL NNSLNPAISE
DNDFNTTTNT FIDSIMAEAN ADNGRFMMEL GKYLRVGFFP DVKTTINLSG PEAYAAAYQD LLMFKEGSMN
IHLIEADLRN FEISKTNISQ STEQEMASLW SFDDARAKAQ FEEYKRNYFE GSLGEDDNLD FSQNIVVDKE
YLLEKISSLA RSSERGYIHY IVQLQGDKIS YEAACNLFAK TPYDSVLFQK NIEDSEIAYY YNPGDGEIQE
IDKYKIPSII SDRPKIKLTF IGHGKDEFNT DIFAGFDVDS LSTEIEAAID LAKEDISPKS IEINLLGCNM
FSYSINVEET YPGKLLLKVK DKISELMPSI SQDSIIVSAN QYEVRINSEG RRELLDHSGE WINKEESGGS
GKMVTGVFKG PNGFEYFAPA NTHNNNIEGQ AIVYQNKFLT LNGKKYYFDN DSKAVTGWQT IDGKKYYFNL
NTAEAATGWQ TIDGKKYYFN LNTAEAATGW QTIDGKKYYF NTNTFIASTG YTSINGKHFY FNTDGIMQIG
VFKGPNGFEY FAPANTDANN IEGQAILYQN KFLTLNGKKY YFGSDSKAVT GLRTIDGKKY YFNTNTAVAV
TGWQTINGKK YYFNTNTSIA STGYTIISGK HFYFNTDGIM QIGVFKGPDG FEYFAPANTD ANNIEGQAIR
YQNRFLYHD NIYYFGNNSK AATGWVTIDG NRYYFEPNTA MGANGYKTID NKNFYFRNGL PQIGVFKGSN
GFEYFAPANT DANNIEGQAI RYQNRFLHLL GKIYYFGNNS KAVTGWQTIN GKVYYFMPDT AMAAAGGLFE
IDGVIYFFGV DGVKAPGIYG
```

FIG. 20

NON-TOXIGENIC CLOSTRIDIUM DIFFICILE SPORES FOR USE IN ORAL VACCINATION

CROSS-REFERENCE TO RELATED APPLICATION(S)

This application claims priority to U.S. Provisional Patent Application No. 62/463,497, filed on Feb. 24, 2017, U.S. Provisional Patent Application No. 62/513,247, filed on May 31, 2017, and U.S. Provisional Patent Application No. 62/588,777, filed on Nov. 20, 2017, each of which are incorporated herein by reference in their entirety.

STATEMENT OF GOVERNMENT SUPPORT

This invention was made with government support under Grant Numbers NIH R21 AI113470 and NIH K01 DK092352 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 29,012 Byte ASCII (Text) file named "17A102PRC-210112-9081-US02-SEQ-LIST-02-26-18.txt," created on Feb. 26, 2018.

TECHNICAL FIELD

The present disclosure relates to genetically modified non-toxigenic *Clostridium difficile* strains, spores, vaccinations, and methods for treating and/or preventing infections caused by *Clostridium difficile*.

BACKGROUND

*Clostridium difficile* is a spore-forming anaerobic and toxin-producing *bacillus*. It is the most common cause of nosocomial antibiotic-associated diarrhea. A CDC study estimated that 29,000 deaths were caused by *Clostridium difficile* in the U.S. in 2011. Antibiotic treatment of *Clostridium difficile* infections may be difficult, due to both to antibiotic resistance and physiological factors of the bacteria (e.g., spore formation and protective effects of the pseudomembrane). Accordingly, there exists a need for effective therapies and prevention of infections caused by *Clostridium difficile*.

SUMMARY OF THE INVENTION

In one aspect, disclosed is a non-toxigenic *Clostridium difficile* strain comprising an immunogenic protein, which comprises a glucosyltranferase domain of *Clostridium difficile* toxin TcdB, a cysteine proteinase domain of *Clostridium difficile* toxin TcdB, and a receptor binding domain of *Clostridium difficile* toxin TcdA. The glucosyltranferase domain of *Clostridium difficile* toxin TcdB comprises a W102A amino acid substitution and a D288N amino acid substitution. Also disclosed in a non-toxigenic *Clostridium difficile* strain comprising a glucosyltransferase domain of *Clostridium difficile* toxin TcdB, a cysteine proteinase domain of *Clostridium difficile* toxin TcdB, a receptor binding domain of *Clostridium difficile* toxin TcdA, and a receptor binding domain of *Clostridium difficile* toxin TcdB. The glucosyltranferase domain of *Clostridium difficile* toxin TcdB comprises a W102A amino acid substitution and a D288N amino acid substitution. The *Clostridium difficile* strains may form spores.

Also disclosed is a vaccine comprising the spores formed by the *Clostridium difficile* strains. Further disclosed is a method of treating or preventing *Clostridium difficile* bacterial infection in a subject in need thereof. In some aspects, the vaccine is administered orally. The vaccine increases levels of anti-TcdA and anti-TcdB IgG antibodies in the subject.

BRIEF DESCRIPTION OF THE DRAWINGS

FIG. 3 shows the domains of Tcd169, which comprise the glucosyltransferase domain (GT) of TcdB, the cysteine proteinase domain (CPD) of TcdB, the receptor binding domain (RBD) of TcdB, and the receptor binding domain (RBD) of TcdA.

FIG. 18 shows the nucleotide sequence that encodes for Tcd169 (4251 bp) (SEQ ID NO.: 2).

FIG. 19 shows the amino acid sequence for Tcd169 (SEQ ID NO.: 3).

FIG. 20 shows the amino acid sequence for Tcd138 (SEQ ID NO.: 4).

DETAILED DESCRIPTION

Figure 1:
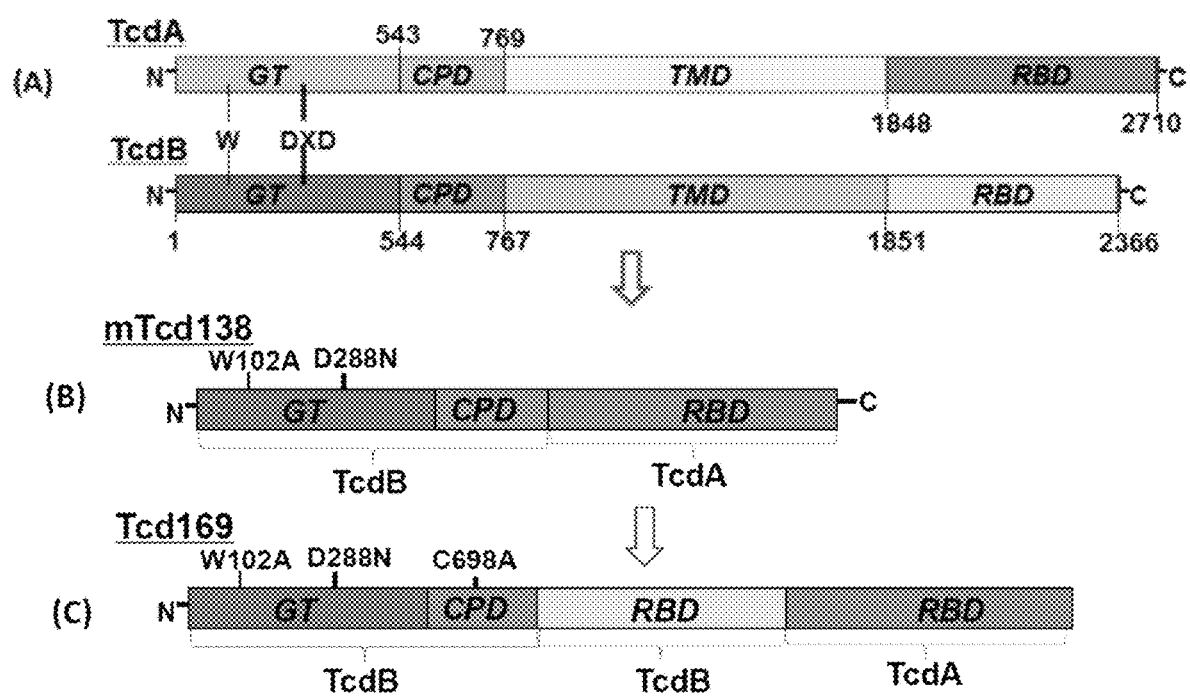
FIG. 1 shows the domains of TcdA and TcdB and construction of mTcd138 and Tcd169. (A) Both toxins share similar domains, including the glucosyltransferase domain (GT), the cysteine proteinase domain (CPD), the translocation domain (TMD) and the receptor binding domain (RBD). The DXD motif and a conserved tryptophan in the GT are involved in the enzymatic activity. (B) mTcd138 (SEQ ID NO.:4) was constructed by fusing the GT and CPD of TcdB (SEQ ID NO.:5) with the RBD of TcdA (SEQ ID NO:6) through the linker (SEQ ID NO.:1). Two point mutations were made in the GT of TcdB, which essentially eliminates the toxicity. (C) Tcd169 (SEQ ID NO.:3) was constructed by fusing the GT and CPD of TcdB (SEQ ID NO.:5), the RBD of TcdB (SEQ ID NO.:7) with the RBD of TcdA (SEQ ID NO:6) through the linker (SEQ ID NO.:1). Two point mutations were made in the GT of TcdB and one point mutation was made in the CPD of TcdB.

Disclosed herein are genetically modified non-toxigenic *Clostridium difficile* strains, spores, vaccinations, and methods for treating and/or preventing bacterial infections. The bacterial infections may be caused by *Clostridium difficile*. The disclosed *Clostridium difficile* spores may be used to prevent a *Clostridium difficile* infection in a subject. The disclosed *Clostridium difficile* strains may be used to treat a *Clostridium difficile* infection in a subject.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "administration" or "administering" as used herein may include the process in which the compositions and vaccines as described herein, alone or in combination with other compounds or compositions, are delivered to a subject. The *Clostridium difficile* spores may be administered in various routes including, but not limited to, oral, mucosal, mucosal nasal, parenteral (including intravenous, intra-arterial, and other appropriate parenteral routes), intrathecally, intramuscularly, subcutaneously, colonically, rectally, and nasally, transcutaneously, among others. The dosing of the *Clostridium difficile* spores described herein to obtain a therapeutic or prophylactic effect may be determined by the circumstances of the subject, as known in the art. The dosing of a subject herein may be accomplished through individual or unit doses of the *Clostridium difficile* spores herein or by a combined or prepackaged or preformulated dose of the *Clostridium difficile* strains.

Administration may depend upon the amount of *Clostridium difficile* spores administered, the number of doses, and duration of treatment. For example, multiple doses of the *Clostridium difficile* spores may be administered. The frequency of administration of the compositions and vaccines may vary depending on any of a variety of factors. The duration of administration of the *Clostridium difficile* spores, e.g., the period of time over which the *Clostridium difficile* spores are administered, may vary, depending on any of a variety of factors, including subject response, etc.

The amount of the *Clostridium difficile* spores administered may vary according to factors such as the degree of susceptibility of the individual, the age, sex, and weight of the individual, idiosyncratic responses of the individual, the dosimetry, and the like. Detectably effective amounts of the *Clostridium difficile* spores of the present disclosure may also vary.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

The term "bacterial strain" and "strain" as used herein, refer to a genetic variant, genetically modified, or subtype of bacteria. The strain may be a genetically modified form of *Clostridium difficile*.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The terms "*Clostridium difficile*", "*C. difficile*", "*C. diff*", and "CDF", and "cdf" as used herein, may be used interchangeably.

The term "genetically modified" as used herein, refers to genetic material that has been altered using genetic engineering techniques. An organism may be genetically modified. Bacteria may be genetically modified.

The term "immunogen", as used herein refers to any substance that may be specifically bound by components of the immune system.

The term "nanoparticle" as used herein refers to particles that are between 1 and 100 nanometers in size.

The term "parenterally," as used herein, refers to modes of administration which include intravenous, intramuscular, intraperitoneal, intrasternal, subcutaneous and intraarticular injection and infusion.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use. "A pharmaceutically acceptable excipient, diluent, carrier and/or adjuvant" as used herein includes one or more such excipients, diluents, carriers, and adjuvants.

As used herein, the term "spore" includes, but is not limited to, a structure produced by bacteria that is resistant to many environmental or induced factors. The spore may be a *Clostridium difficile* spore.

As used herein, the term "subject," "patient," or "organism" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like. The subject may have a bacterial infection. The subject may have a bacterial infection caused by *Clostridium difficile*. The subject may be taking antibiotics. The subject may be taking antibiotics for a bacterial infection that is caused by bacteria other than *Clostridium difficile*. The subject may be at risk for an infection caused by *Clostridium difficile*.

The "therapeutically effective amount" for purposes herein may be determined by such considerations as are known in the art. A therapeutically effective amount of a compound may include the amount necessary to provide a therapeutically effective result in vivo. The amount of the compound or composition must be effective to achieve a response, including but not limited to a total prevention of (e.g., protection against) of a condition, improved survival rate or more rapid recovery, improvement or elimination of symptoms associated with the condition (such as cancer), or other indicators as are selected as appropriate measures by those skilled in the art. As used herein, a suitable single dose size includes a dose that is capable of preventing or alleviating (reducing or eliminating) a symptom in a subject when administered one or more times over a suitable time period. The "therapeutically effective amount" of a compound or composition as described herein may depend on the route of administration, type of subject being treated, and the physical characteristics of the subject. These factors and their relationship to dose are well known to one of skill in the medicinal art, unless otherwise indicated.

The term "toxin" as used herein, may refer to small molecules, peptides, or proteins that are capable of causing disease on contact with or absorption by body tissues interacting with biological macromolecules such as enzymes or cellular receptors. Toxins may be produced by microorganisms. Toxins may be produced by *Clostridium difficile*. Toxins may be virulence determinants responsible for microbial pathogenicity. Toxins may be virulence determinants responsible for evasion of the host immune response.

As used herein, "treat", "treatment", "treating", and the like refer to acting upon a condition with an agent to affect the condition by improving or altering it. The condition includes, but is not limited to infection, such as those caused by bacteria. The bacterial infection may be caused by *Clostridium difficile*. The aforementioned terms cover one or more treatments of a condition in a subject (e.g., a mammal, typically a human or non-human animal of veterinary interest), and include: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., treating bacterial infections caused by *Clostridium difficile*).

As used herein, the term "virulence factors" include, but are not limited to the ability of bacteria to cause disease in terms of the number of infecting bacteria, the route of entry into the body, the effects of host defense mechanisms, and intrinsic characteristics of the bacteria called. A "hyper-virulent" bacterial strain may be more difficult to treat. A "hyper-virulent" bacterial strain may cause symptoms that are worse than an infection from a bacterial strain that is not hyper-virulent. A "hyper-virulent" bacterial strain may be more deadly.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Immunogenic Proteins

Pathogenic *Clostridium difficile* infection strains produce multiple toxins. *Clostridium difficile* produces toxins. Two *Clostridium difficile* infection toxins are enterotoxin (*Clostridium difficile* toxin A (TcdA)) and cytotoxin (*Clostridium difficile* toxin B (TcdB)). Toxins A and B are glucosyltransferases that target and inactivate the Rho family of GTPases. TcdB may induce actin depolymerization by a mechanism correlated with a decrease in the ADP-ribosylation of the low molecular mass GTP-binding Rho proteins.

In one aspect, disclosed are immunogenic proteins that comprise one or more domains from *Clostridium difficile* toxins. The immunogenic protein may be a chimeric protein. The immunogenic protein may comprise one or more domains from *Clostridium difficile* toxin A (TcdA). The immunogenic protein may comprise the glucosyltransferase domain (GT) from TcdA. The immunogenic protein may comprise the cysteine proteinase domain (CPD) from TcdA. The immunogenic protein may comprise the receptor binding domain (RBD) from TcdA. The immunogenic protein may contain one or more domains from *Clostridium difficile* toxin B (TcdB). The immunogenic protein may comprise the glucosyltransferase domain (GT) from TcdB. The immunogenic protein may comprise the cysteine proteinase domain (CPD) from TcdB. The immunogenic protein may comprise the receptor binding domain (RBD) from TcdB.

The one or more domains may be connected by an amino acid linker. The amino acid linker may be the amino acid sequence of GGSG (SEQ ID NO.: 1).

In some embodiments, the immunogenic protein comprises the glucosyltransferase domain of TcdB, cysteine proteinase domain of TcdB, receptor binding domain of TcdB, and the receptor binding domain of TcdA. The domains may be connected by an amino acid linker. The linker may be the amino acid linker GGSG. In some embodiments, there is a W102A amino acid substitution and a D288N amino acid substitution in the GT of TcdB and a C698A amino acid substitution in the CPD of TcdB. The W102A amino acid substitution and D288N amino acid substitution in the GT of TcdB eliminate toxicity of TcdB. The immunogenic protein may be encoded by the nucleotide sequence as set forth in SEQ ID NO.: 2. The immunogenic protein may be Tcd169 (SEQ ID NO.: 3).

In some embodiments, the immunogenic protein comprises the glucosyltransferase domain of TcdB, the cysteine proteinase domain of TcdB, and the receptor binding domain (RBD) of TcdA. The domains may be connected by an amino acid linker. The linker may be the amino acid linker GGSG. In some embodiments, there is a W102A amino acid substitution and a D288N amino acid substitution in the GT of TcdB and a C698A amino acid substitution in the CPD of TcdB. The W102A amino acid substitution and D288N amino acid substitution in the GT of TcdB eliminate toxicity of TcdB. The immunogenic protein may be Tcd138 (SEQ ID NO.: 4). The immunogenic protein may be encoded by a nucleotide sequence that encodes Tcd138 (SEQ ID NO.: 4).

3. Non-Toxigenic *Clostridium difficile* Strains

In one aspect, disclosed are non-toxigenic *Clostridium difficile* strains. The non-toxigenic *Clostridium difficile* strain may be *Clostridium difficile* 85 strain (NTCD). In one aspect, disclosed are genetically modified non-toxigenic *Clostridium difficile* strains. The non-toxigenic *Clostridium difficile* strain may comprise immunogenic proteins that comprise one or more domains from *Clostridium difficile* toxins. The non-toxigenic *Clostridium difficile* strain may comprise the immunogenic protein Tcd169. The non-toxigenic *Clostridium difficile* strain may be NTCD_Tcd169. The non-toxigenic *Clostridium difficile* strain may comprise the immunogenic protein Tcd138. The non-toxigenic *Clostridium difficile* strain may be NTCD_Tcd138. The disclosed non-toxigenic *Clostridium difficile* strains may form spores. The spores may be administered to a subject to treat or prevent a *Clostridium difficile* infection.

4. Pharmaceutical Compositions

The disclosed *Clostridium difficile* spores may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of *Clostridium difficile* spores of the disclosure (e.g., a composition and vaccine) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of disclosed *Clostridium difficile* spores may be, but is not limited to, about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed *Clostridium difficile* spores are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, transdermal, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active and 50% to 99.99% of one or more carriers. Compositions for parenteral administration typically include 0.1% to 10% of actives and 90% to 99.9% of a carrier including a diluent and a solvent.

Compositions for oral administration can have various dosage forms. The oral dosage form may be a vaccination. The oral dosage form may be solid forms including tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid compositions, which may be administered orally, may include a disclosed compositions, and vaccines and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed *Clostridium difficile* spores may be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. The carrier of the topical composition preferably aids penetration of the compounds into the skin. The carrier may further include one or more optional components. Transdermal administration may be used to facilitate delivery.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

In an embodiment, the pharmaceutical composition may include human breast milk. The active pharmaceutical ingredient may be a component of human breast milk. The human breast milk may thus be administered to a subject in need of the active pharmaceutical ingredient.

5. Method of Treatment and Method of Preventing Bacterial Infection

The disclosed *Clostridium difficile* spores may be used in methods for treatment of bacterial infections. The *Clostridium difficile* spores as disclosed herein may be used for preventing bacterial infections in a subject. The methods of treatment may comprise administering to a subject in need of such treatment, a composition comprising a therapeutically effective amount of the *Clostridium difficile* spores disclosed herein. Spores formed by the NTCD_Tcd169 strain may be administered to treat or prevent *Clostridium difficile* infection. Spores formed by the NTCD_Tcd138 strain may be administered to treat or prevent *Clostridium difficile* infection. Spores formed by the NTCD_Tcd169 strain may be administered to treat or prevent *Clostridium difficile* infection. Spores formed by the NTCD_Tcd169 strain may be administered in combination with spores formed by the NTCD_Tcd138 strain to treat or prevent *Clostridium difficile* infection. The *Clostridium difficile* infection treated by the methods disclosed herein may be caused by a hyper-virulent *Clostridium difficile* strain.

*Clostridium difficile* colonization may be targeted by the administration of the *Clostridium difficile* spores disclosed herein. *Clostridium difficile* growth factors may be targeted by the administration of the *Clostridium difficile* spores disclosed herein. *Clostridium difficile* toxins may be targeted by the administration of the *Clostridium difficile* spores disclosed herein.

a. Bacterial Infections

Although bacteria may not be harmful, and in some cases may be beneficial, bacteria may also lead to infection. Bacterial infections can affect multiple organs and body systems including, but not limited to, gastrointestinal tract, intestines, skin, mucous membranes, blood, lungs, kidneys, urinary tract, eyes, heart, meninges, respiratory tract, genitals, stomach, bone, connective tissue, and tissue surrounding organs. Bacterial infections may affect more than one organ or body system. Bacterial infections may be systemic. Bacterial infections may be asymptomatic. Bacterial infections may cause a variety of symptoms including, but not limited to, fever, inflammation, wounds that do not heal, weeping wounds, skin rash, red bumps on the skin, abscesses, swollen lymph nodes, nausea, diarrhea, headaches, earaches, sore throat, fatigue, low blood pressure, hyperventilation, weak and rapid pulse, local or systemic pain, and muscle aches. Bacterial infections may cause death. Subjects with co-morbidities or a compromised immune system may be more susceptible to bacterial infections.

The diagnosis of a bacterial infection may include, but are not limited to, symptomatic diagnostics, microbial culture, microscopy, biochemical tests, PCR based diagnostics, and metagenomics sequencing. A microbial examination may include sample collection, microbial cultivation, identification, and test of antibiotic susceptibility. The diagnosis may include gram staining of the bacterial culture. The diagnosis may include a coagulase test of the bacterial culture. The diagnosis may include a catalase test of the bacterial culture. The diagnosis may include blood tests. The blood tests may include, but are not limited to, a full blood count, measurement of C-reactive protein, measurement of procalcitonin, and measurement of rapid plasma reagin. The diagnosis may include ELISA. The diagnosis may include PCR. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The determination of bacteria growing on an agar plate or in a nutrient broth may determine the bacteria responsible for the subject's infection. Discs containing antibiotic compounds may be placed on the agar plates. The antibiotic compounds may kill the bacteria growing on the plate. The antibiotics that are effective at killing the bacteria may aid in diagnosing the type of bacterial infection.

Samples for diagnosing a bacterial infection may be obtained from the subject in need of treatment. The sample for testing may be from the site of the infection. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and/or other body fluids. Multiple samples may be taken from the subject. Multiple samples may be taken around the site of a prosthesis or medical device.

i. *Clostridium difficile* Infections

The bacterial infection may be *Clostridium difficile*. When stressed, *Clostridium difficile* may produce spores. The *Clostridium difficile* spores may be able to tolerate extreme conditions that the active bacteria cannot tolerate. A bacterial spore may make the bacteria more resistant to environmental factors or induced factors that the bacteria may be subjected to. Spores may help bacteria survive by being resistant to extreme changes in the bacteria's habitat. Extreme changes in the bacteria's habitat may include extreme temperatures, lack of moisture/drought, or being exposed to chemicals and radiation. Bacterial spores may be able to survive at low nutrient levels. Bacterial spores may be resistant to antibiotics and disinfectants. Bacterial spores may be resistant to elimination. Bacteria that produce spores may be pathogenic. Spore-forming bacteria may be in the *Bacillus* and *Clostridium* species. Spore-forming bacteria may be found in other species of bacteria. There are different types of spores, including but not limited to endospores, exospores, and spore-like structures called microbial cysts. Spores may aid the bacteria in survival and serve as protection for the cell.

*Clostridium difficile* may be transmitted from person to person by the fecal-oral route. *Clostridium difficile* may be shed in feces. Any surface, device, or material (e.g., toilets, bathing tubs, and electronic rectal thermometers) that becomes contaminated with feces may serve as a reservoir for the *Clostridium difficile* spores. *Clostridium difficile* spores may be transferred to subjects via the hands of healthcare personnel who have touched a contaminated surface or item. *Clostridium difficile* may live for long periods of time on surfaces. *Clostridium difficile* spores may be heat-resistant. *Clostridium difficile* may not be not killed by alcohol-based hand cleansers or routine surface cleaning. *Clostridium difficile* spores may survive in clinical environments for long periods. Once spores are ingested, their acid-resistance may allow them to pass through the stomach unscathed. The *Clostridium difficile* spores may germinate and multiply into vegetative cells in the colon upon exposure to bile acids.

Symptoms of a *Clostridium difficile* infection may include, but are not limited to watery diarrhea, fever, loss of appetite, nausea, abdominal pain/tenderness. Conditions that may result from a *Clostridium difficile* infection may include, but are not limited to pseudomembranous colitis (PMC), toxic megacolon, perforations of the colon, and sepsis. A *Clostridium difficile* infection may be deadly.

Antibiotic therapy for various infections may have the adverse effect of disrupting the normal balance of the gut flora. *Clostridium difficile* may grow in the presence of an antibiotic. *Clostridium difficile* may grow in the absence of other bacteria. The growth of *Clostridium difficile* may cause a *Clostridium difficile* infection in a subject. Administering a vaccination against *Clostridium difficile* to a subject may prevent or treat a *Clostridium difficile* infection.

The treatment or prevention of *Clostridium difficile* infections may comprise immunization. After immunization, the subject may develop the ability to quickly respond to a subsequent encounter with an immunogen because of immunological memory. This may be a function of the adaptive immune system. Therefore, by exposing a subject to an immunogen in a controlled way, the subject's body may protect itself in the presence of an immunogen. The immunogen may be a *Clostridium difficile* immunogen. The immunization may fortify a subject's immune system against *Clostridium difficile* infections. Immunizing a subject with *Clostridium difficile* spores may prepare the subject's immune system to respond to *Clostridium difficile*. Immunizing a subject with *Clostridium difficile* spores may prevent a *Clostridium difficile* infection. Immunizing a subject with a *Clostridium difficile* spores may treat a *Clostridium difficile* infection.

The treatment or prevention of *Clostridium difficile* infections may comprise immunization with spores formed by the NTCD_Tcd169 strain. The treatment or prevention of *Clostridium difficile* infections may comprise immunization with spores formed by the NTCD_Tcd138 strain. The treatment or prevention of *Clostridium difficile* infections may comprise immunization with spores formed by the NTCD_Tcd169 strain in combination with spores formed by the NTCD_Tcd138 strain. Immunization with the spores disclosed herein may increases levels of anti-TcdA and anti-TcdB IgG antibodies in the subject.

Immunization may be through various techniques. The route of immunization may include, but is not limited to oral, nasal mucosal, sublingual, subcutaneous, intramuscular, intradermal, or Immunization may be through oral vaccination. Vaccines against bacteria that cause infections may prepare the subject's immune system, thus helping to fight or prevent an infection. The vaccine may comprise the spores disclosed herein. The vaccine may comprise the spores disclosed herein and a pharmaceutically acceptable excipient. The vaccine may comprise synthetic oligodeoxynucleotides (ODNs). The synthetic oligonucleotides may comprise unmethylated CpG motifs (CpG ODNs) trigger cells that express Toll-like receptor 9 to mount an innate immune response. CpG ODNs may improve the function of professional antigen-presenting cells. CpG ODNs may boost the generation of humoral and cellular vaccine-specific immune responses.

In some embodiments, the vaccination is an oral vaccination. The oral vaccination may comprise *Clostridium difficile* spores. Oral vaccination may be the most effective method of protecting the gut against infection. Oral vaccination may expose the vaccination to proteolytic or hydrolyzing digestive enzymes, bile salts, extreme pH, rapid movement of contents, and limited access to the mucosal wall.

b. Modes of Administration

Methods of treatment may include any number of modes of administering the disclosed *Clostridium difficile* spores. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally, for parenteral administration, the agent can be in the form of an aqueous, lipid, oily or other kind of solution or suspension or even administered in the form of liposomes or nano-suspensions.

c. Combination Therapies

Additional therapeutic agent(s) may be administered simultaneously or sequentially with the disclosed *Clostridium difficile* spores. Sequential administration includes administration before or after the disclosed *Clostridium difficile* spores. In some embodiments, the additional therapeutic agent or agents may be administered in the same composition as the disclosed *Clostridium difficile* spores. In other embodiments, there may be an interval of time between administration of the additional therapeutic agent and the disclosed *Clostridium difficile* spores. In some embodiments, administration of an additional therapeutic agent with a disclosed compositions and vaccines may allow lower doses of the other therapeutic agents and administration at less frequent intervals. When used in combination with one or more other active ingredients, the *Clostridium difficile* spores of the present invention and the other active ingredients may be used in lower doses than when each is used singly. Accordingly, the *Clostridium difficile* spores of the present invention include those that contain one or more other active ingredients, in addition to *Clostridium difficile* spores. The above combinations include combinations of *Clostridium difficile* spores of the present invention not only with one other active compound, but also with two or more other active compounds.

d. Evaluation of Treatment

The efficacy of the methods of treatment with *Clostridium difficile* spores disclosed herein may be measured. The status of the bacterial infection may be monitored. The efficacy of the methods of treatment disclosed herein may be evaluated by the same or similar methods as used for diagnosis of the bacterial infection.

Evaluating the efficacy of the methods of treatment with the *Clostridium difficile* spores disclosed herein or monitoring the bacterial infection may include, but are not limited to, symptomatic diagnostics, microbial culture, microscopy, biochemical tests, PCR based tests, and metagenomics sequencing. A microbial examination may include sample collection, microbial cultivation, identification, and test of antibiotic susceptibility. The evaluation or monitoring may include gram staining of the bacterial culture. The evaluation or monitoring may include a coagulase test of the bacterial culture. The evaluation or monitoring may include a catalase test of the bacterial culture. The evaluation or monitoring may include blood tests. The blood tests may include, but are not limited to, a full blood count, measurement of C-reactive protein, measurement of procalcitonin, and measurement of rapid plasma reagin. The evaluation or monitoring may include ELISA. The evaluation or monitoring may include PCR. The sample may be grown on an agar plate. The sample may be grown in nutrient broth. The growth conditions may include varying factors (e.g., type of growth medium, nutrients, selective compounds, antibiotics, temperature, pH level, oxygen level) to determine the type of bacteria growing. The presence, decreased presence, or lack of bacteria growing on an agar plate or in a nutrient broth may determine that the bacterial infection is improving or has been eradicated.

Samples for determining the efficacy of the methods of treatment with the *Clostridium difficile* spores disclosed herein or monitoring the bacterial infection, may be obtained from the subject. The sample for testing may be from the site of the infection, or the site where the infection was previously present. A sample for testing may be obtained from the subject by swabbing of the skin, throat, or nose. A sample for testing may be obtained from the subject by collecting pus or fluids from wounds, abscesses, or other skin infections. A sample for testing may be obtained from the subject by collecting body fluids. The body fluids may include blood, sputum, urine, and other body fluids. Multiple samples may be taken from the subject. Multiple samples may be taken around the site of a prosthesis or medical device.

The evaluation of the efficacy of methods of treatment with the *Clostridium difficile* spores disclosed herein or monitoring of the bacterial infection may indicate that the subject requires continued treatment with *Clostridium difficile* spores disclosed herein. The evaluation of the efficacy of methods of treatment with *Clostridium difficile* spores disclosed herein or monitoring of the bacterial infection may indicate the eradication of the bacterial infection in the subject. The eradication of the bacterial infection may indicate that the subject no longer requires treatment with the *Clostridium difficile* spores disclosed herein.

6. Kits

The *Clostridium difficile* spores may be included in kits comprising the compositions and vaccines; and information, instructions, or both that use of the kit will provide treatment for medical conditions in mammals (particularly humans). The kit may include an additional pharmaceutical composition for use in combination therapy. The kit may include buffers, reagents, or other components to facilitate the mode of administration. The kit may include materials to facilitate oral administration. The kit may include materials to facilitate nasal mucousal administration. The kit may include materials that facilitate sublingual administration. The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The *Clostridium difficile* spores of the invention will be better understood by reference to the following examples, which are intended as an illustration of and not a limitation upon the scope of the invention.

7. Examples

Example 1. Construction of Tcd169

Figure 2:
FIG. 2 shows the domains of Tcd138, which comprise the glucosyltransferase domain (GT) of TcdB, the cysteine proteinase domain (CPD) of TcdB, and the receptor binding domain (RBD) of TcdA.
Figure 3:
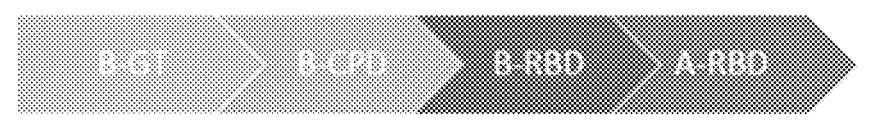
Figure 4:
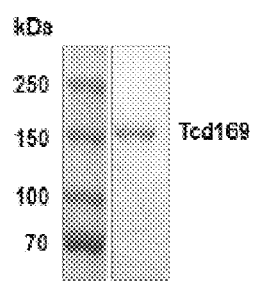
FIG. 4 shows the expression and purification of Tcd169. Gene sequence encoding Tcd169 was synthesized and cloned in *Bacillus megatarium*. Protein Tcd169 was purified from bacterial lysate by Ni-affinity chromatography and gel filtration, and analyzed by SDS-PAGE.

A recombinant fusion protein, designated mTcd138 (FIGS. 1B, 2) was generated. mTcd138 contains the glucosyltransferase and cysteine proteinase domains of TcdB and the RBD of TcdA. Protein mTcd138 was expressed it in *Bacillus megaterium*. To ensure mTcd138 is atoxic, two point mutations (FIGS. 1B, 2) were made in the glucosyltransferase domain of TcdB, which essentially eliminates mTcd138 toxicity in vitro and in vivo. To enhance the immunogenicity, mTcd138 was fused with the RBD of TcdB bridged with an amino acid linker (for example, GGSG), resulting in protein Tcd169 (FIGS. 1C, 3). The Chimeric DNA encoding Tcd169 was ligated into *B. megaterium* expression vector which adds a C-terminal His-tag to the chimeric proteins. Tcd169 was purified from bacterial lysate by Ni-affinity chromatography and gel filtration (FIG. 4).

Figure 5:
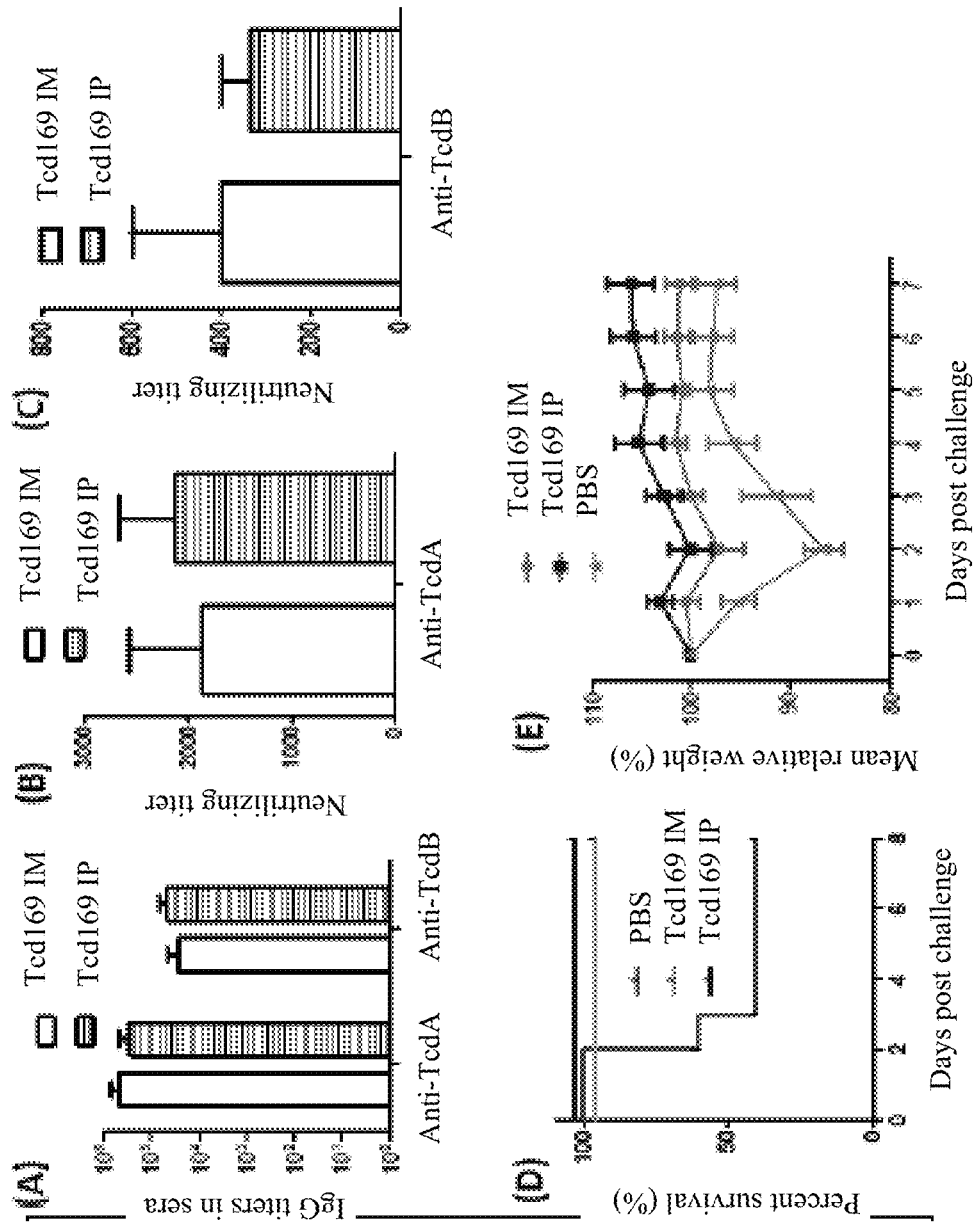
FIG. 5 shows the protective responses of Tcd169 immunization (IM or IP) in mice. Groups of C57 BL/6 mice (n=10) were immunized with Tcd169 (10 μg) or PBS in the presence of alum for 3 times at 14-day intervals (IM or IP). Anti-toxin IgG titers (A) and anti-toxin neutralizing titers (B, C) in sera from third immunization were measured. Seven days after third immunization, mice were given antibiotic mixture in drinking water for 4 days, switched to regular water for 2 days, and were given one dose of clindamycin (10 mg/kg) one day before infection with $10^6$ of *C. difficile* UK6 spores by gavage. After infection, mouse survivals (P=0.0486 between PBS and Tcd169 IM/Tcd169 IP groups) (D), and mean relative weight changes (E) of different groups were recorded. The neutralizing titer is expressed as the maximum dilution of the sera that inhibits Vero cell rounding caused by toxin at a given concentration. This given concentration is the minimum toxin dose causing cell rounding after a 16 h of toxin exposure, i.e., 2.5 and 0.1 ng/ml for TcdA and TcdB, respectively.

Example 2. Tcd169 Immunization Induces Protective Responses Against Both Toxins and Infection with an Epidemic *C. difficile* Strain Immunization with Tcd169 via intraperitoneal (i.p), intramuscular (i.m.) routes induced similar levels of IgG antibody responses against both toxins (FIG. 5A). Tcd169 immunization induced potent neutralizing antibodies against both toxins (FIGS. 5B & 5C). Protection efficacy of Tcd169 immunization was evaluated in a mouse model of CDI. After three immunizations (10 µg Tcd169 per immunization with Alum as adjuvant, at 14-day intervals) via i.p. or i.m. route, mice were challenged with $10^6$ spores of *C. difficile* UK6 (BI/NAP1/027). In vehicle-immunized mice, significant disease symptoms including weight loss (FIG. 5E), severe diarrhea in all mice; approximately 40% of mice succumbed by day 3 (FIG. 5D). In contrast, all Tcd169-immunized mice survived (FIG. 5D) and showed no signs of weight loss (FIG. 5E).

Example 3. Expression of mTcd138 in Non-Toxigenic *C. difficile* 85 Strain (NTCD), Resulting in Strain NTCD_Tcd138

Figure 6:
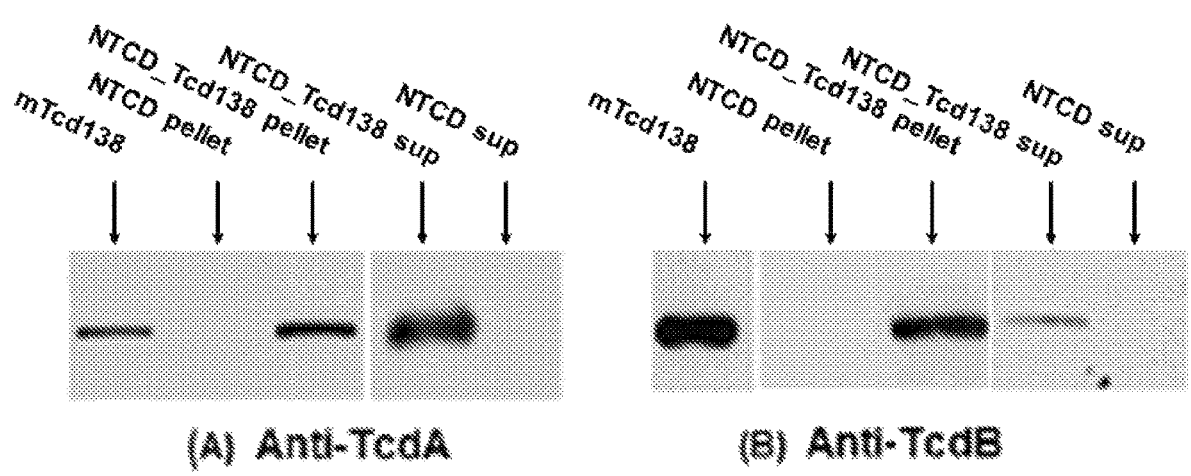
FIG. 6 shows the expression of mTcd138 in non-toxigenic *C. difficile* 85 strain (NTCD). Western blot analysis of supernatants and pellets of NTCD_Tcd138 and NTCD (mTcd138 as positive control) using anti-TcdA (A) or anti-TcdB (B) antibodies.

By engineering NTCD to express the mTcd138 construct, two independent methods of reducing CDI were combined in one treatment. The gene encoding mTcd138 was cloned in the *E. coli*-*C. difficile* shuttle vector pRPF144 in *E. coli* Stb12 (Invitrogen). Conjugative transfer of plasmid from *E. coli* to NTCD was performed. Intermediate *E. coli* Stb12 harboring the conjugative plasmid pRPF144-mTcd138 was used as a donor strain. Expression of mTcd138 in NTCD was verified by western blot analysis (FIG. 6).

Figure 7:
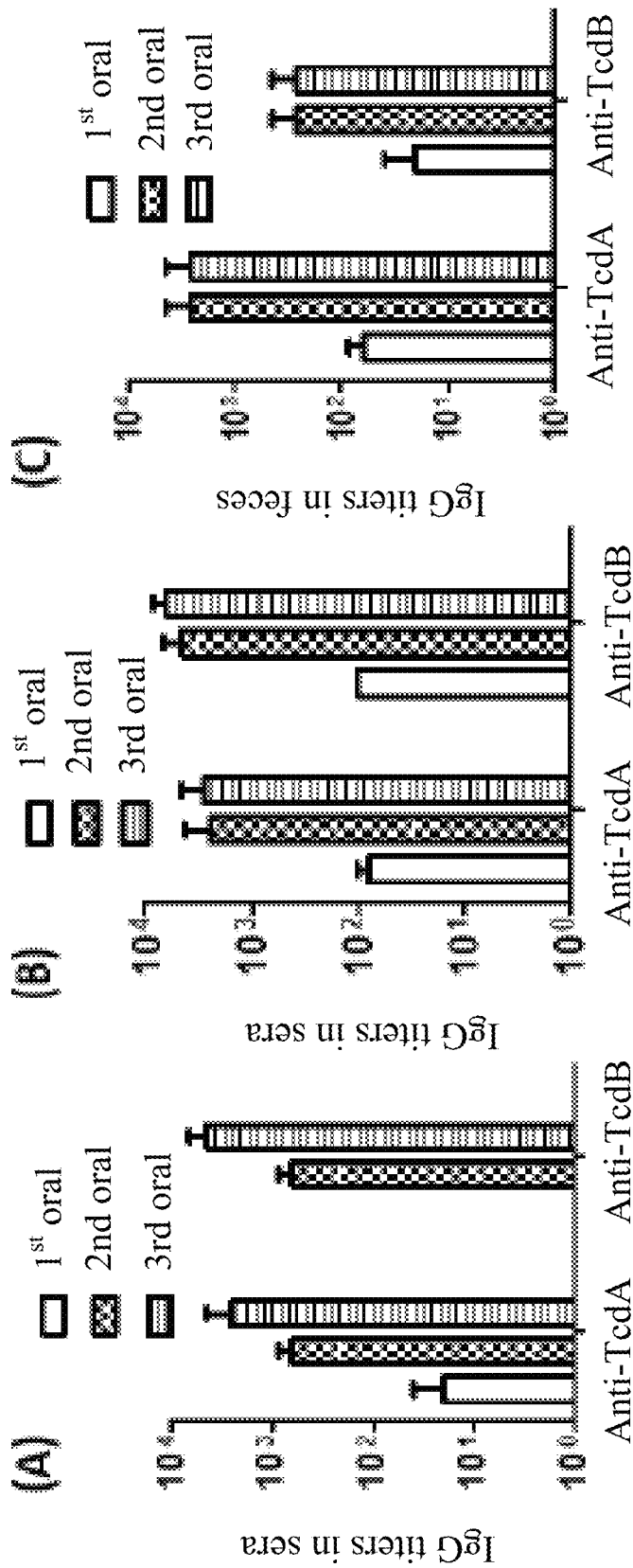
FIG. 7 shows that oral immunization of mice with NTCD_Tcd138 spores induces mucosal and systemic toxin-specific antibody responses. Groups of C57 BL/6 mice (N=10) were orally immunized with NTCD_mTcd138 ($2 \times 10^6$ spores/immunization for 3 times at 14-day intervals). Sera and feces were collected after each immunization. Before use, feces were dissolved (0.1 g/ml) in PBS containing proteinase inhibitors. Anti-TcdA/anti-TcdB IgG titers in sera (A), anti-TcdA/anti-TcdB IgA titers in sera (B) or in feces (C) were determined by ELISA.
Figure 8:
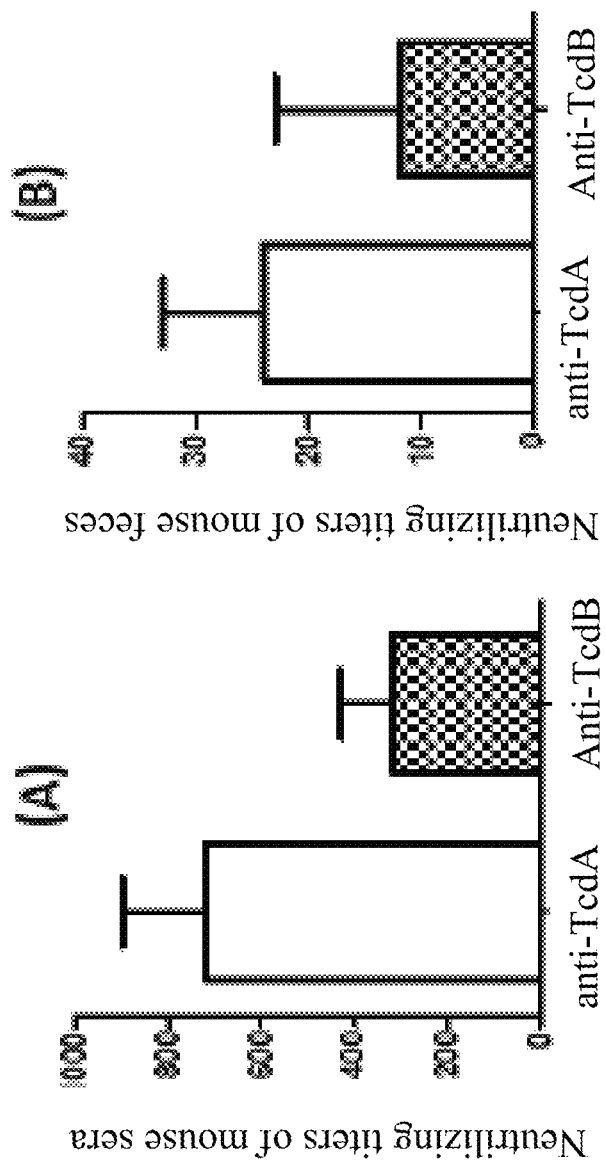
FIG. 8 shows anti-toxin neutralizing titers of sera or feces from mice orally immunized with NTCD_Tcd138 spores. Vero cells were used to determine in vitro neutralizing activities of sera (A) or feces (B). The neutralizing titer is expressed as the maximum dilution of the sera that inhibits cell rounding caused by toxin at a given concentration. This given concentration is the minimum toxin dose causing cell rounding after a 16 h of toxin exposure, i.e., 2.5 and 0.1 ng/ml for TcdA and TcdB, respectively.
Figure 9:
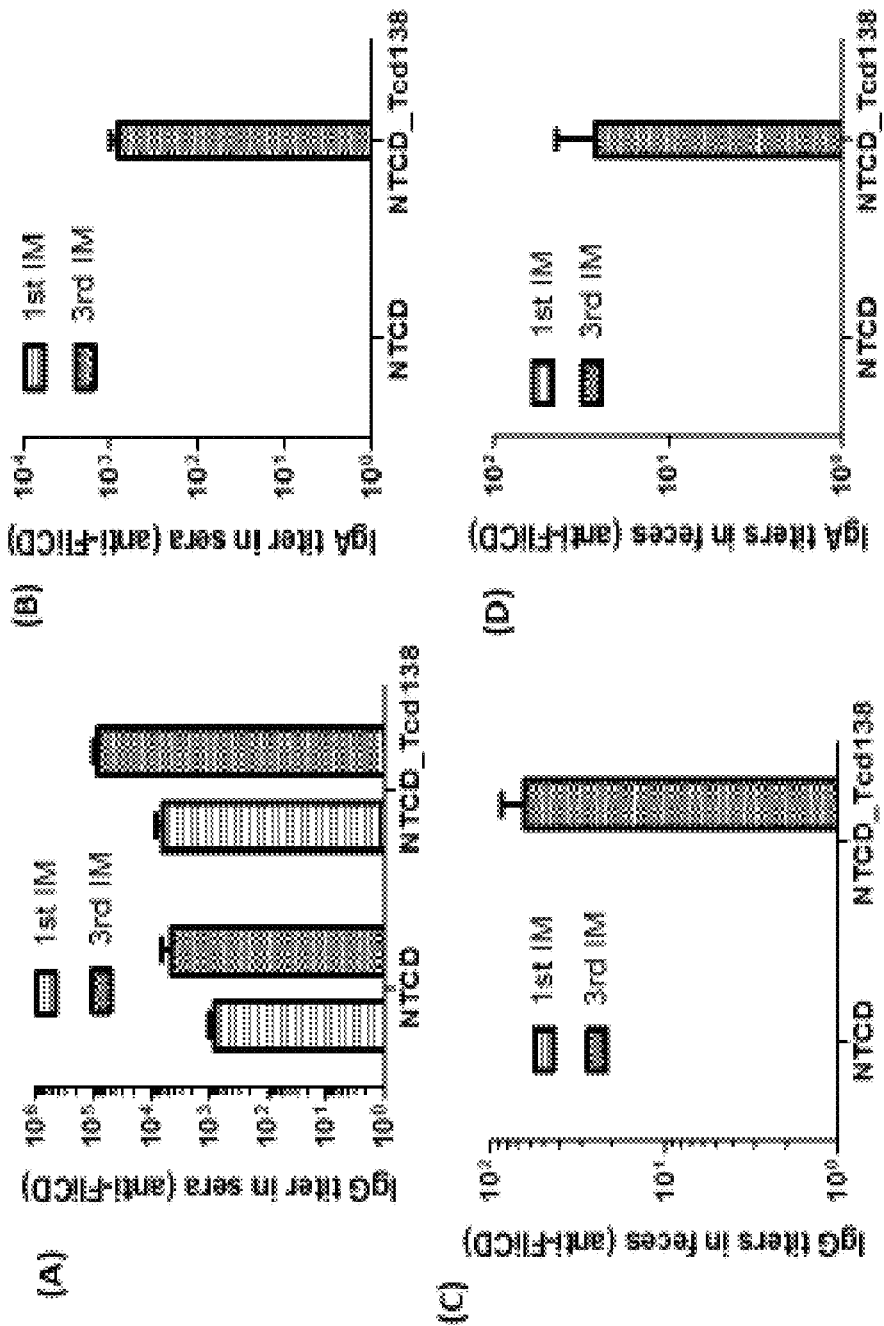
FIG. 9 shows that oral immunization of mice with NTCD_Tcd138 or NTCD spores induces mucosal and systemic antibody responses against FliCD. Groups of C57 BL/6 mice (N=10) were orally immunized with NTCD_mTcd138 or NTCD at $2 \times 10^6$ spores for 3 times at 14-day intervals. Sera and feces were collected after each immunization. Before use, feces were dissolved (0.1 g/ml) in PBS with proteinase inhibitors. Anti-FliCD IgG titers in sera (A) or feces (C), and anti-FliCD IgA titers in sera (B) or feces (D) were determined by ELISA.
Figure 10:
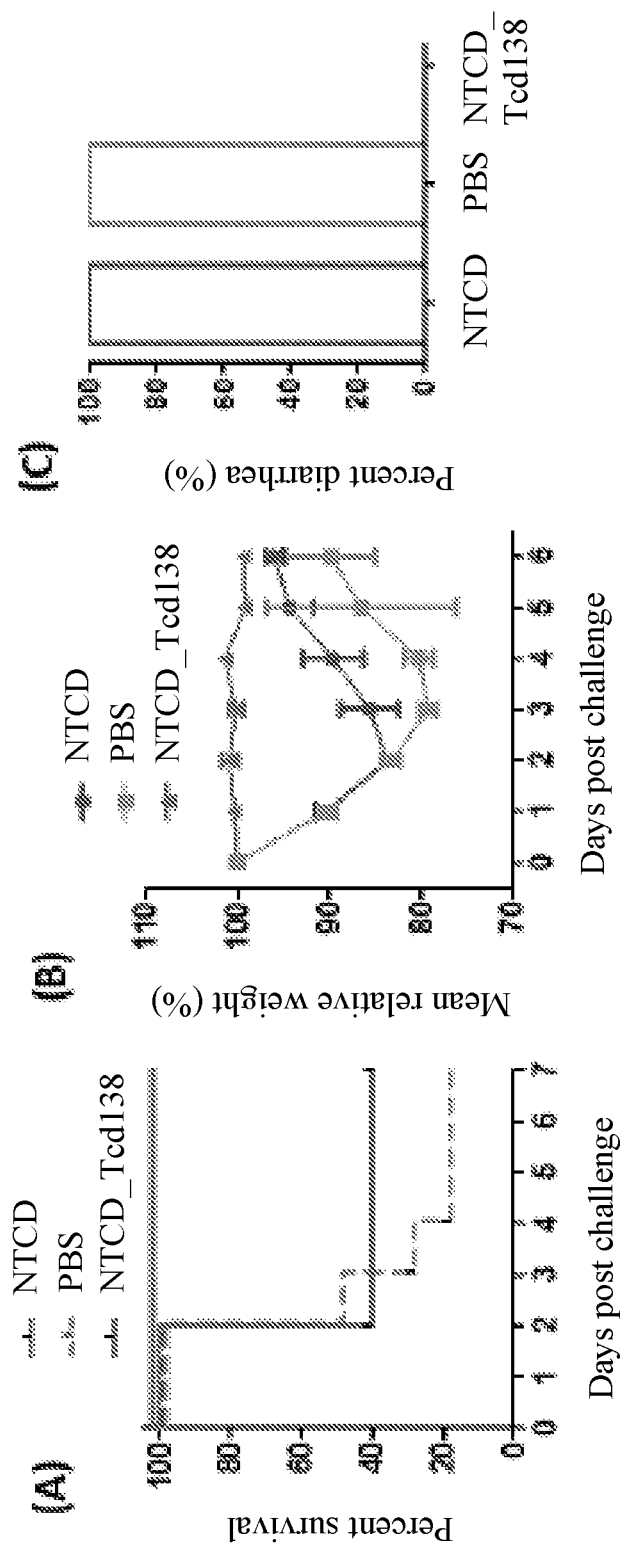
FIG. 10 shows that oral immunization with NTCD_Tcd138 spores provides full protection to mice against infection with a hyper-virulent C. difficile strain UK6. Groups of mice (N=10) were orally immunized with NTCD, or NTCD_Tcd138 ($2 \times 10^6$ spores in 200 μl PBS) or PBS (200 μl) for 3 times at 14-day intervals. Seven days after third immunization, mice were given antibiotic mixture in drinking water for 4-days, switched to regular water for 2 days, and were given one dose of clindamycin (10 mg/kg) before infection with $10^6$ spores C. difficile UK6 by gavage. Mice were monitored, and mouse survivals (P=0.495 between groups PBS and NTCD; P=0.0002 between groups PBS and NTCD_Tcd138) (A), mean relative weight changes (B) and frequency of diarrhea (C) of different groups were recorded.
Figure 11:
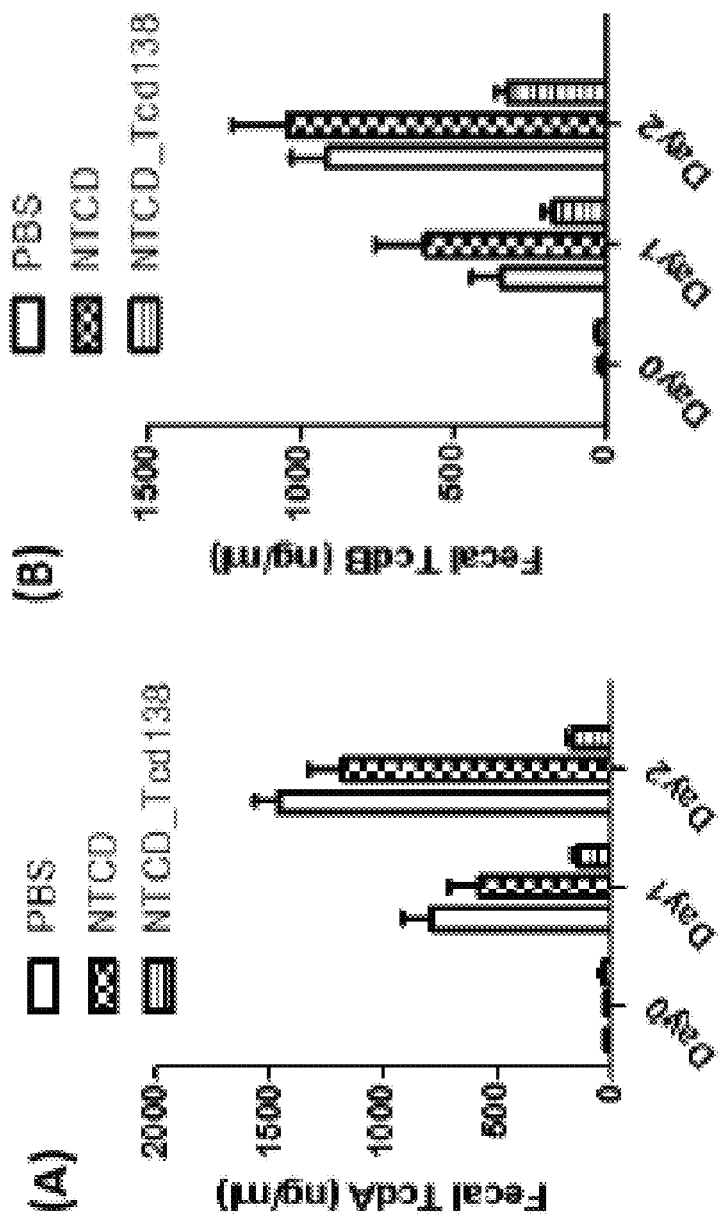
FIG. 11 shows fecal toxin levels of mice orally immunized with NTCD, NTCD_Tcd138 spores or PBS followed by infection with C. difficile UK6 spores. Groups of mice (N=10) were orally immunized with NTCD, or NTCD_Tcd138 ($2 \times 10^6$ spores in 200 l PBS) or PBS (200 μl) for 3 times at 14-day intervals. Seven days after third immunization, mice were given antibiotic mixture in drinking water for 4-days, switched to water for days, and were given one dose of clindamycin (10 mg/kg) before infection with $10^6$ spores C. difficile UK6 by gavage. Feces were collected on post infection days 0,1, and 2, dissolved (0.1 g/ml) in PBS with proteinase inhibitors. TcdA (A) or TcdB (B) levels in feces were determined by ELISA.

Example 4. Oral Immunization of Mice with NTCD_Tcd138 Spores Induces Mucosal and Systemic Toxin-Specific Antibody Responses, and Protects Mice from Infection with a Hyper-Virulent *C. difficile* Strain Oral immunization of mice with NTCD_Tcd138 ($2\times10^6$ spores per immunization for 3 times at 14-day intervals) induced both IgG and IgA antibody responses specific for both toxins in sera (FIGS. 7A & 7B), as well as IgA antibodies specific for both toxins in feces (FIG. 7C). NTCD_Tcd138 immunization also induced neutralizing antibodies against both toxins (FIG. 8). To determine whether NTCD or NTCD_Tcd138 immunization can induce anti-*C. difficile* responses, a fusion protein containing full-length of *C. difficile* flagellin proteins FliC and FliD were generated (designated FliCD), and measured anti-FliCD antibody levels in sera and feces from NTCD- or NTCD_Tcd138-immunized mice. It was found that in comparison with NTCD, NTCD_Tcd138 immunization could induce higher levels of anti-FliCD IgG/IgA responses in both sera (FIGS. 9A & 9B) and feces (FIGS. 9C & 9D). Protection efficacy of NTCD_Tcd138 was further evaluated in a mouse model of CDI. After three oral immunizations ($2\times10^6$ spores per immunization for 3 times at 14-day intervals), mice were challenged with $10^6$ spores of *C. difficile* UK6. In vehicle (PBS)-immunized mice, significant disease symptoms including weight loss (FIG. 10B) and severe diarrhea (FIG. 10C) were evident in all mice; approximately 20% of mice succumbed by day 4 (FIG. 10A). In contrast, NTCD_Tcd138-immunized mice were fully protected and showed no signs of disease at any stage (FIG. 10). Immunization with NTCD-only showed slight, but not significant protection (FIGS. 10A & 10B) against *C. difficile* challenge. NTCD_Tcd138-immunized mice secreted a significantly less amount of toxins compared to NTCD-only or PBS immunization groups (FIG. 11).

Figure 12:
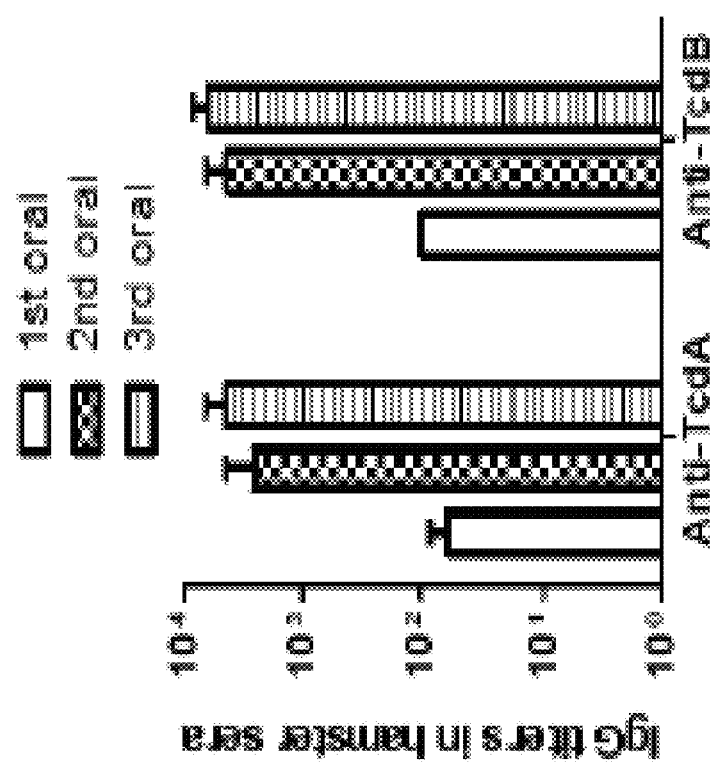
FIG. 12 shows that oral immunization of hamsters with NTCD_Tcd138 spores induces systemic toxin-specific antibody responses. Groups of golden Syrian hamsters (N=10) were orally immunized with NTCD_mTcd138 at $2 \times 10^6$ spores for 3 times at 14-day intervals. Sera and feces were collected after each immunization. Anti-TcdA/anti-TcdB IgG titers in sera were determined by ELISA.
Figure 13:
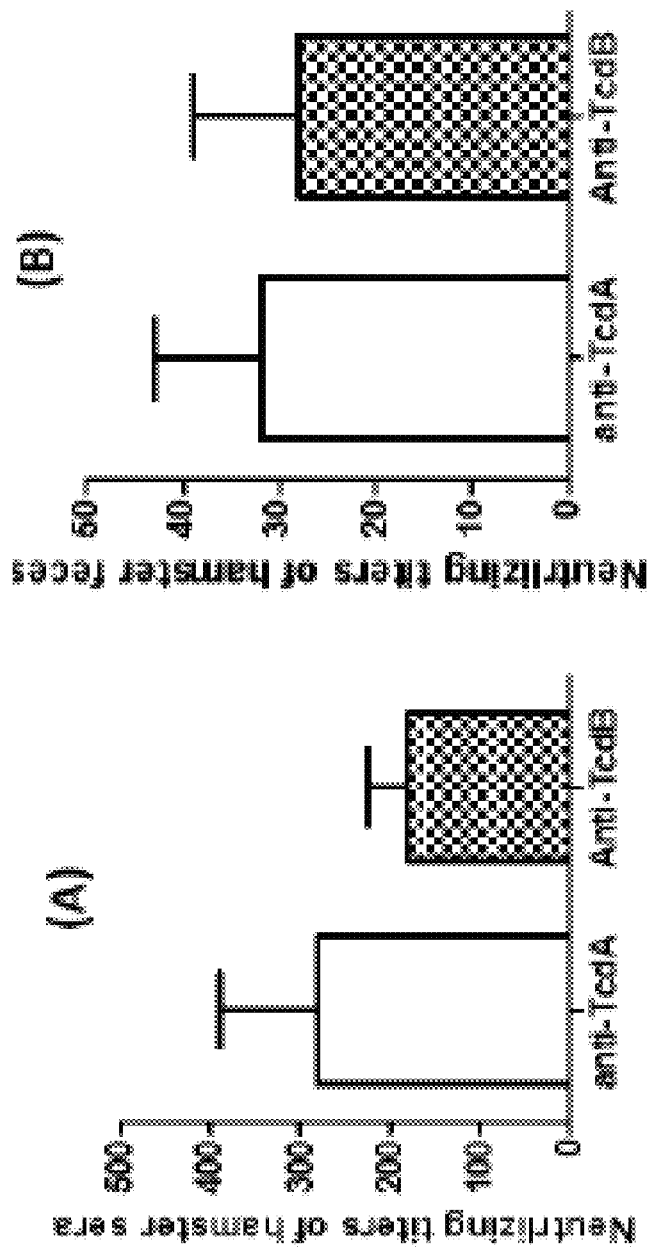
FIG. 13 shows anti-toxin neutralizing titers of sera or feces from hamsters orally immunized with NTCD_Tcd138 spores. Vero cells were used to determine in vitro neutralizing activities of sera (A) or feces (B). The neutralizing titer is expressed as the maximum dilution of the sera that inhibits cell rounding caused by toxin at a given concentration. This given concentration is the minimum toxin dose causing cell rounding after a 16 h of toxin exposure, i.e., 2.5 and 0.1 ng/ml for TcdA and TcdB, respectively.
Figure 14:
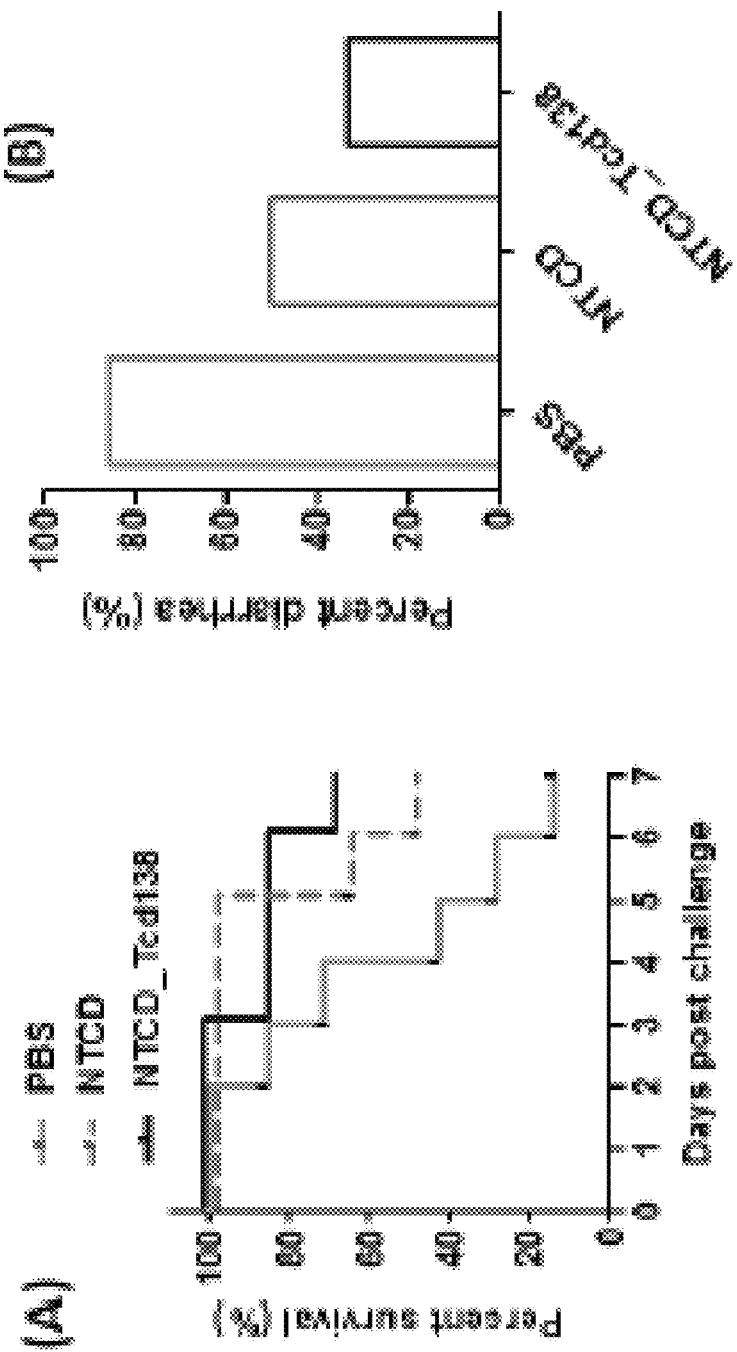
FIG. 14 shows that oral immunization with NTCD_Tcd138 spores provides significant protection to hamsters against infection with a virulent C. difficile UK6 strain at a dose of 200-fold of the lethal infection dose. Groups of hamsters (N=10) were orally immunized with NTCD, or NTCD_Tcd138 ($2 \times 10^6$ spores in 200 μl PBS) or PBS (200 μl) for 3 times at 14-day intervals. Seven days after third immunization, hamsters were given clindamycin (IP, 40 mg/kg/day for 2 days), followed by infection with $2 \times 10^4$ C. difficile UK1 spores by gavage. Hamsters were monitored, and survivals (P=0.0754 between groups PBS and NTCD; P=0.0453 between groups PBS and NTCD_Tcd138) (A) and diarrhea frequency (B) recorded.
Figure 15:
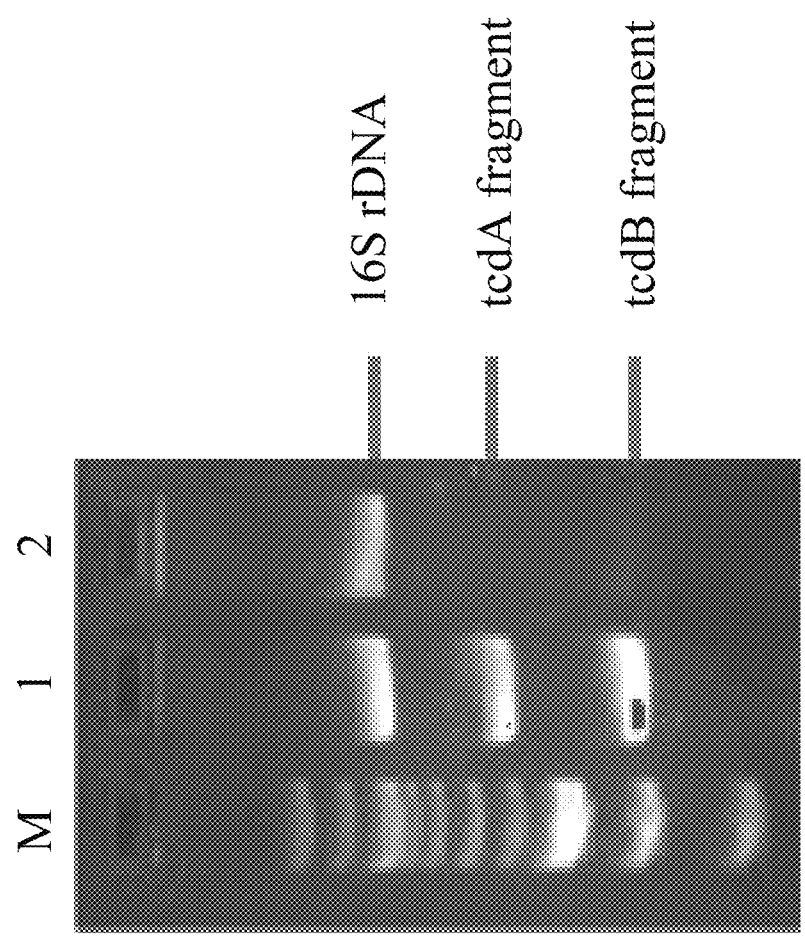
FIG. 15 shows the toxin gene profiles of two selected C. difficile strains. Lane 1, tcdA$^+$, tcdB$^+$; Lane 2, non-toxigenic C. difficile; Lane M: 100-bp DNA marker. A rapid 3-plex PCR was developed for the detection of tcdA, tcdB and 16s rDNA. 5 μl of 12-24 hrs of C. difficile culture was used as template.

Example 5. Oral Immunization of Hamsters with NTCD_Tcd138 Spores Induces Protective Responses Against Both Toxins and Infection with a Hyper-Virulent *C. difficile* Strain The immunogenicity and protection efficacy of NTCD_Tcd138 was evaluated in hamsters. Oral immunization of hamsters with NTCD_Tcd138 ($2\times10^6$ spores per immunization for 3 times at 14-day intervals) induced similar levels of anti-TcdA and anti-TcdB IgG antibodies in sera (FIG. 12). Anti-TcdA/TcdB IgA antibodies could not be measured due to the lack of hamster-raised anti-IgA antibodies. Neutralizing antibodies against both toxins were detected in both sera and feces (FIG. 13). Hamsters are extremely sensitive to *C. difficile* infection, and usually die within 2 to 3 days of infection at a dose of 100 spores. Therefore, hamster is an ideal animal to test the strength of vaccine candidates against CDI. To evaluate the protection strength of NTCD_Tcd138, the immunized hamsters were challenged ($2\times10^6$ spores of NTCD_Tcd138 or NTCD per immunization for 3 times at 14-day intervals) with a hyper-virulent *C. difficile* strain UK6 at $2\times10^4$ spores/hamster, which is 200-fold of the lethal *C. difficile* infection dose (100 spores). Oral immunization with NTCD_Tcd138 spores provided significant protection to hamsters against such a high challenge dose (FIG. 14). In agreement with results in mice (FIGS. 11A & 11B), immunization of hamsters with NTCD-only spores also provided protection though not significant (FIG. 15).

Example 6. Rapid Identification of Toxigenic/Non-Toxigenic *C. difficile* Strains by Multiplex PCR To rapidly identify toxigenic/non-toxigenic *C. difficile* strains, a simple and fast 3-plex PCR method was developed to identify tcdA, tcdB and 16s rDNA specific for *C. difficile*. In this method, 5 µl of 12-24 hrs of *C. difficile* culture was used as template (FIG. 15). This method will be used to distinguish toxigenic *C. difficile* strains from non-toxigenic *C. difficile* strains.

Figure 16:
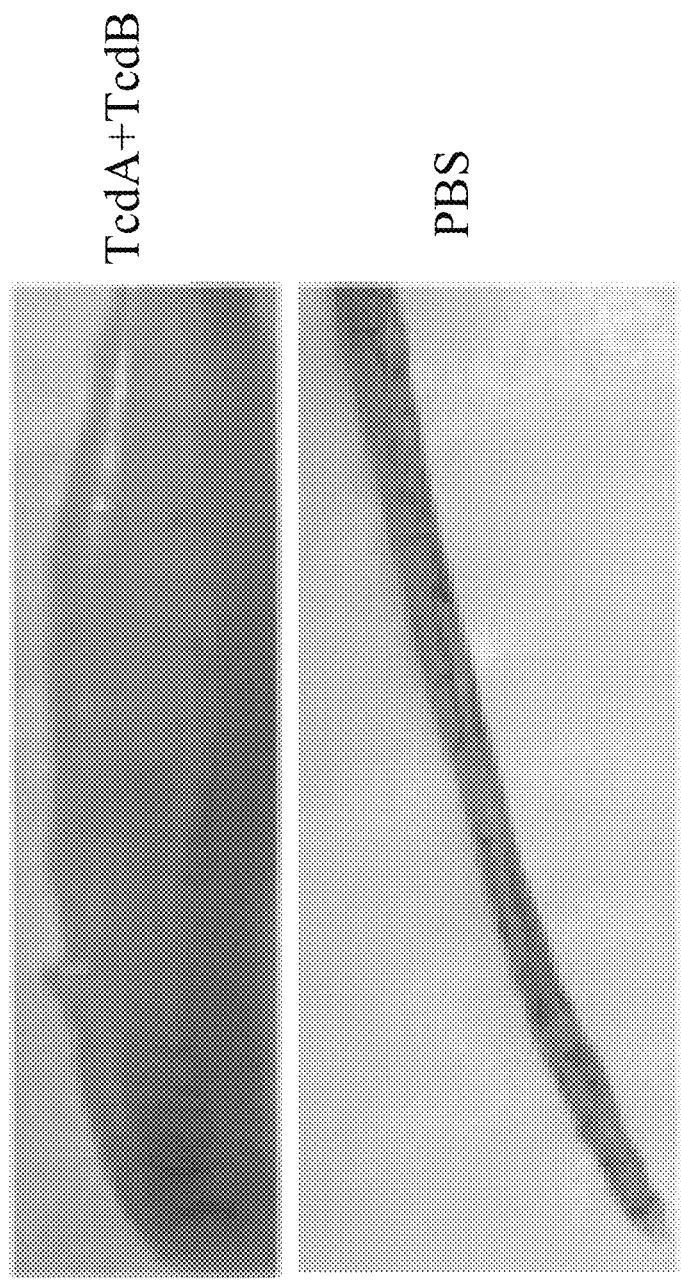
FIG. 16 shows the colonic inflammation and injury caused by direct intra-rectal instillation of TcdA/TcdB. A 5F infant feeding tube was inserted 2.5 cm up the colon. 100 μl of TcdA (10 μg)+TcdB (10 μg) or PBS was slowly administered. 4 or 5 hours later mice were euthanized and dissected to analyze the toxin-mediated effects on the colon.

Example 7. Establishment of Novel and More Efficient Mouse Model of *C. difficile* Toxin Exposure A mouse model of *C. difficile* toxin exposure was developed. A 5F infant feeding tube catheter with side ports (Mallinckrodt Inc., St. Louis, Mo.; catalogue no. 85771) was inserted 2.5 cm up the colon. At this point, 100 µl of TcdA (10 µg)+TcdB (10 µg) or PBS was slowly administered over 30 s while pressure was applied to the anal area to prevent leakage. Following injection of the solution, the tube was slowly removed and the rectal pressure was maintained for a further 30 s. Four hours later, mice were euthanized and dissected to analyze the toxin-mediated effects on the colon. The administration of TcdA/TcdB triggered dramatic colonic inflammation (FIG. 16) and neutrophil and macrophage infiltration. This "intra-rectal toxin instillation" approach will be used to determine immunization protection against toxin challenge via rectum.

Example 8. Construct Strain NTCD_Tcd169

Figure 17:
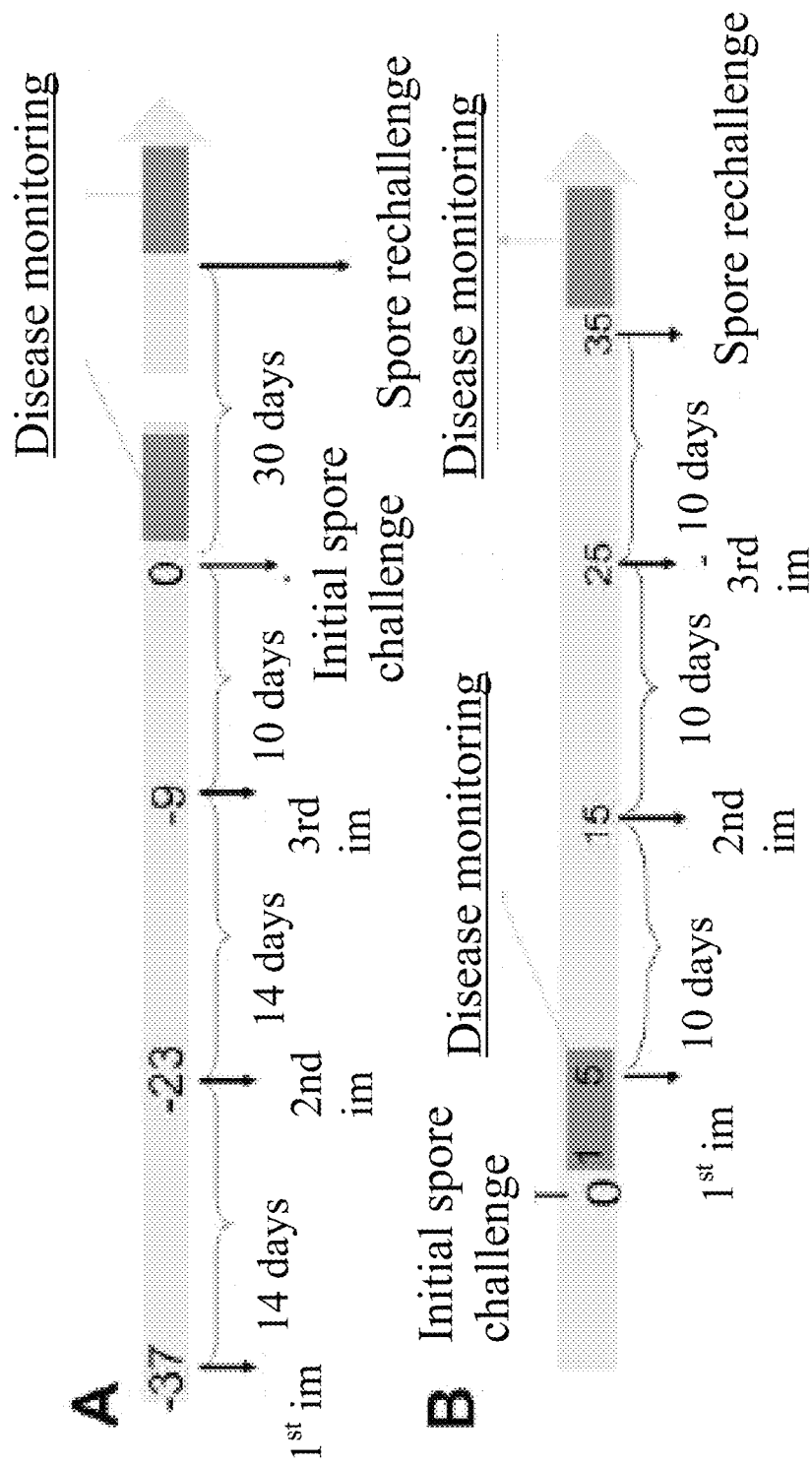
FIG. 17 shows immunization and challenge schemes for CDI relapse models in mice. (A) After 3 immunizations mice will be pretreated with antibiotic mixture, challenged with C. difficile UK6 spores, and monitored for about a week. Thirty days after initial spore challenge, survived mice will be again treated with antibiotics mixture followed by infection with C. difficile UK6 spores and monitoring. (B) Non-immunized naïve mice will be pretreated with antibiotic mixture, challenged with C. difficile UK6 spores, and monitored for about a week. Starting on post-infection day 5, mice will be immunized for 3 times at 10-day intervals. Ten days after third immunization, mice will be again treated with antibiotics mixture followed by infection with C. difficile UK6 spores and monitoring.

The gene encoding Tcd169 was cloned in the *E. coli-C. difficile* shuttle vector pRPF144 in *E. coli* Stb12 (Invitrogen). Conjugative transfer of plasmids from *E. coli* to non-toxigenic *C. difficile* 85 (NTCD) was performed. Intermediate *E. coli* Stb12 harboring the conjugative plasmid pRPF144-Tcd169 was used as a donor strain. Expression of Tcd169 in NTCD will be verified by western-blot analysis. The resultant strains will be designated NTCD_Tcd169. The spores of these strains will be prepared.

Example 9. Determine Protection Against Systemic Toxin Challenge

A potent antibody response will be generated, that protects mice against challenge with a lethal dose of TcdA/TcdB (100 ng for each toxin). One week after the third immunization, mice will be challenged IP with a lethal dose of TcdA, TcdB or a mixture of TcdA and TcdB (100 ng for each toxin), and monitored for 72 hrs. If the protection is not optimal, dose optimization experiments will be performed.

For oral immunization with NTCD_Tcd169 spores and adjuvants will be mixed and given to mice by gavage.

Example 10. In Vitro Neutralization Titers for Both Systemic and Mucosal Antibodies, and Anti-Adherence Capability of Antibody Against Adhesion of *C. difficile* to Intestinal Epithelial Cells The neutralizing titers against TcdA and TcdB, and anti-adherence capability of sera and mucosal samples against adhesion of *C. difficile* to intestinal epithelial cells will be determined.

Example 11. Protection Against Systemic Challenge of the Toxins

Protection against systemic toxin challenge will be performed. $LD_{50}$im will be used as the standard challenge dose to assess the levels of the protection against systemic toxin challenge induced by the mucosal immunization for each immunogen. The mucosal immunizations may induce a similar level of protection as do parenteral immunization, in which 50% of mice will survive from challenge with $LD_{50}$im dose of each wild type toxin, or two toxins given together. Should greater than 50% of mice die, a dose optimization will be performed as described below.

Example 12. Protection Against Mucosal Challenge with Toxins

In the above experiments, the generation of mucosal IgA and IgG antibodies against toxins will be examined. It will be assessed whether these antibodies produced in the gut can protect mice against toxin-mediated destruction of the mucosa. The "intra-rectal toxin instillation" approach will be used.

One week after the third immunization, mice (immunized with immunogens or placebo) will be directly injected with 10 μg of TcdA or TcdB or both (10 μg each) in a volume of 100 μl via rectum. Four hours later, mice will be euthanized and the colon will be carefully removed. Toxin-induced fluid accumulation will be quantitated as the ratio of weight to length. In addition to assessing the fluid accumulation, the pathological signs, such as neutrophil infiltration and villus damage, will be evaluated histologically. Histopathological and neutrophil myeloperoxidase (MPO) activity assays will be performed to evaluate mucosal damage and neutrophil infiltration. The resected colons will be fixed in 4% formaldehyde buffered with PBS and then embedded with paraffin. Deparaffinized 6-μm-thick sections will be stained with haematoxylin and eosin (H&E) for histological analysis, and the tissue injuries will be blindly scored by a histologist. Histological grading criteria will be as follows: 0, minimal infiltration of lymphocytes, plasma cells, and eosinophils; 1+, mild infiltration of lymphocytes, plasma cells, neutrophils, and eosinophils plus mild congestion of the mucosa with or without hyperplasia of gut-associated lymphoid tissue; 2+, moderate infiltrations of mixed inflammatory cells, moderate congestion and edema of the lamina propria, with or without goblet cell hyperplasia, individual surface cell necrosis or vacuolization, and crypt dilatation; 3+, severe inflammation, congestion, edema, and hemorrhage in the mucosa, surface cell necrosis, or degeneration with erosions or ulcers. To measure MPO activities, a portion of the resected colon will be homogenized in 1 ml of 50 mM potassium phosphate buffer with 0.5% hexadecyl trimethyl ammonium bromide and 5 mM EDTA. MPO activities in a centrifuged supernatant will be determined using a substrate o-phenylenediamine in a solution containing 0.05% of $H_2O_2$ followed by measuring absorbance at 490 nm.

Example 13. Dose Optimization

Dose optimization of antigens will follow by performing doubling and halving the optimized doses determined in previous examples for 4 immunogens. If an adjuvant is used, e.g. dmLT, the same amount of the adjuvant will be mixed together with the immunogen before injection. For each dose and route of immunization, both systemic and mucosal IgG and IgA response will be monitored and their neutralizing titers will be measured. The lowest amount of antigen required to induce the highest level of serum and mucosal antibody response for each immunogen will be established.

Example 14. Protection Against Recurrent CDI in Mice

CDI has become increasingly difficult to manage due, in part, to the ineffectiveness of current antibiotic regimens which are associated with high relapse rates. The efficacy of top-ranked regimens of immunization in preventing disease recurrence in a spore-induced mouse CDI recurrence model which was developed previously will be evaluated. To induce CDI relapse, surviving mice will be given antibiotic cocktail treatment followed by oral gavage of *C. difficile* UK6 spores ($10^6$/mouse) 30 days after the primary infection. The immunization and challenge scheme is illustrated in FIG. 17A. To assess whether immunization also protects against disease relapse in naïve animals that recovered from CDI, surviving mice will be immunized after their recovery from the initial CDI as illustrated (FIG. 17B).

Example 15. Protection Against CDI in Hamsters

After three immunizations, hamsters will be pretreated with clindamycin followed by challenged with 100 to $10^4$ *C. difficile* UK6 spores. Weight changes, diarrhea and modality will be recorded. After infection, fecal samples will be collected for 10 days to compare spore secretion and toxin levels in feces from immunized and non-immunized groups.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the present disclosure are set out in the following numbered clauses:

Clause 1. A non-toxigenic *Clostridium difficile* strain comprising:
   a) an immunogenic protein comprising
      i) a glucosyltranferase domain of *Clostridium difficile* toxin TcdB;
      ii) a cysteine proteinase domain of *Clostridium difficile* toxin TcdB; and
      iii) a receptor binding domain of *Clostridium difficile* toxin TcdA,
   wherein the glucosyltranferase domain of *Clostridium difficile* toxin TcdB comprises a W102A amino acid substitution and a D288N amino acid substitution.

Clause 2. The non-toxigenic *Clostridium difficile* strain of clause 1, wherein the immunogenic protein comprises the amino acid sequence of SEQ ID NO.: 4.

Clause 3. The non-toxigenic *Clostridium difficile* strain of clause 2, wherein the strain is non-toxigenic *Clostridium difficile* strain 138 (NTCD_Tcd138).

Clause 4. The non-toxigenic *Clostridium difficile* strain of clause 1, wherein the *Clostridium difficile* form spores.

Clause 5. A non-toxigenic *Clostridium difficile* strain comprising:
   i) a glucosyltranferase domain of *Clostridium difficile* toxin TcdB;
   ii) a cysteine proteinase domain of *Clostridium difficile* toxin TcdB;
   iii) a receptor binding domain of *Clostridium difficile* toxin TcdA; and
   iv) a receptor binding domain of *Clostridium difficile* toxin TcdB,
   wherein the glucosyltranferase domain of *Clostridium difficile* toxin TcdB comprises a W102A amino acid substitution and a D288N amino acid substitution.

Clause 6. The non-toxigenic *Clostridium difficile* strain of clause 5, wherein the immunogenic protein comprises the amino acid sequence of SEQ ID NO.: 3.

Clause 7. The non-toxigenic *Clostridium difficile* strain of clause 6, wherein the strain is non-toxigenic *Clostridium difficile* strain 169 (NTCD_Tcd169).

Clause 8. The non-toxigenic *Clostridium difficile* strains of clause 5, wherein the *Clostridium difficile* form spores.

Clause 9. A vaccine comprising the *Clostridium difficile* spores of clause 4 or clause 8 and a pharmaceutically acceptable excipient.

Clause 10. A vaccine comprising the *Clostridium difficile* spores of clause 4 and clause 8 and a pharmaceutically acceptable carrier.

Clause 11. A method of treating or preventing *Clostridium difficile* bacterial infection in a subject in need thereof, the method comprising administering the vaccine of clause 9 or clause 10.

Clause 12. The method of clause 11, wherein the vaccine is administered orally.

Clause 13. The method of clause 11, wherein the vaccine increases levels of anti-TcdA and anti-TcdB IgG antibodies in the subject.

Clause 14. The method of clause 11, wherein the *Clostridium difficile* bacterial infection is caused by a hypervirulent strain of *Clostridium difficile*.

Deposit Information. Applicant desposited the non-toxigenic *Clostridium difficile* strains NTCD_Tcd138 and NTCD_Tcd169, with the American Type Culture Collection (ATCC), 10801 University Boulevard Manassas, VA 20110 USA, in compliance the Budapest Treaty and in compliance with 37 C.F.R. §§ 1.801-1.809 on Nov. 21, 2019. The ATTC Acecession No. for NTCD_Tcd1138 is PTA-126151 and the ATCC Accession NO. for NTCD_Tcd169 is PTA-126152. This deposit shall be made available to persons determined by the Commissioner of Patents and Trademarks to be entitled thereto under 37 CFR § 1.14 and 15 USC § 122.

What is claimed is:

1. A non-toxigenic *Clostridium difficile* strain comprising:
   a) an immunogenic protein comprising
      i) a glucosyltransferase domain of *Clostridium difficile* toxin TcdB;
      ii) a cysteine proteinase domain of *Clostridium difficile* toxin TcdB; and
      iii) a receptor binding domain of *Clostridium difficile* toxin TcdA,
   wherein the glucosyltransferase domain of *Clostridium difficile* toxin TcdB comprises a W102A amino acid substitution and a D288N amino acid substitution when compared to SEQ ID NO.: 5.

2. The non-toxigenic *Clostridium difficile* strain of claim 1, wherein the immunogenic protein comprises the amino acid sequence of SEQ ID NO.: 4.

3. The non-toxigenic *Clostridium difficile* strain of claim 2, wherein the strain is non-toxigenic *Clostridium difficile* strain 138 (NTCD_Tcd138).

4. The non-toxigenic *Clostridium difficile* strain of claim 1, wherein the *Clostridium difficile* form spores.

5. A non-toxigenic *Clostridium difficile* strain comprising:
   a) an immunogenic protein comprising
      i) a glucosyltransferase domain of *Clostridium difficile* toxin TcdB;
      ii) a cysteine proteinase domain of *Clostridium difficile* toxin TcdB;
      iii) a receptor binding domain of *Clostridium difficile* toxin TcdA; and
      iv) a receptor binding domain of *Clostridium difficile* toxin TcdB,
   wherein the glucosyltransferase domain of *Clostridium difficile* toxin TcdB comprises a W102A amino acid substitution and a D288N amino acid substitution and the cysteine proteinase domain of *Clostridium difficile* toxin TcdB comprises a C698A amino acid substitution when compared to SEQ ID NO.: 5.

6. The non-toxigenic *Clostridium difficile* strain of claim 5, wherein the immunogenic protein comprises the amino acid sequence of SEQ ID NO.: 3.

7. The non-toxigenic *Clostridium difficile* strain of claim 6, wherein the strain is non-toxigenic *Clostridium difficile* strain 169 (NTCD_Tcd169).

8. The non-toxigenic *Clostridium difficile* strain of claim 5, wherein the *Clostridium difficile* form spores.

9. A vaccine comprising the *Clostridium difficile* spores of claim 4 and a pharmaceutically acceptable excipient or carrier.

10. A vaccine comprising the *Clostridium difficile* spores of claim 8 and a pharmaceutically acceptable excipient or carrier.

11. A method of treating or preventing *Clostridium difficile* bacterial infection in a subject in need thereof, the method comprising administering the vaccine of claim 9.

12. The method of claim 11, wherein the vaccine is administered orally.

13. The method of claim 11, wherein the vaccine increases levels of anti-TcdA and anti-TcdB IgG antibodies in the subject.

14. The method of claim 11, wherein the *Clostridium difficile* bacterial infection is caused by a hyper-virulent strain of *Clostridium difficile*.

15. The non-toxigenic *Clostridium difficile* strain of claim 1, wherein the glucosyltransferase domain of *Clostridium difficile* toxin TcdB is positioned immediately upstream of the cysteine proteinase domain of *Clostridium difficile* toxin TcdB, wherein the amino acid sequence of the linked glucosyltransferase domain of *Clostridium difficile* toxin TcdB and the cysteine proteinase domain of *Clostridium difficile* toxin TcdB is set forth in SEQ ID NO.: 8; and wherein the receptor binding domain of *Clostridium difficile* toxin TcdA comprises the amino acid sequence of SEQ ID NO.: 6.

16. The non-toxigenic *Clostridium difficile* strain of claim 5, wherein the glucosyltransferase domain of *Clostridium difficile* toxin TcdB is positioned immediately upstream of the cysteine proteinase domain of *Clostridium difficile* toxin TcdB, wherein the amino acid sequence of the linked glucosyltransferase domain of *Clostridium difficile* toxin TcdB and the cysteine proteinase domain of *Clostridium difficile* toxin TcdB is set forth in SEQ ID NO.: 9; wherein the receptor binding domain of *Clostridium difficile* toxin TcdA comprises the amino acid sequence of SEQ ID NO.: 6; and wherein the receptor binding domain of *Clostridium difficile* toxin TcdB comprises the amino acid sequence of SEQ ID NO.: 7.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Gly Gly Ser Gly
1

<210> SEQ ID NO 2
<211> LENGTH: 4251
```

<212> TYPE: DNA
<213> ORGANISM: Artificial Sequence
<220> FEATURE:
<223> OTHER INFORMATION: Synthetic

<400> SEQUENCE: 2

| | | | | | |
|---|---|---|---|---|---|
| atgagtttag | ttaatagaaa | acagttagaa | aaaatggcaa | atgtaagatt | tcgtactcaa | 60 |
| gaagatgaat | atgttgcaat | attggatgct | ttagaagaat | atcataatat | gtcagagaat | 120 |
| actgtagtcg | aaaaatattt | aaaattaaaa | gatataaata | gtttaacaga | tatttatata | 180 |
| gatacatata | aaaaatctgg | tagaaataaa | gccttaaaaa | aatttaagga | atatctagtt | 240 |
| acagaagtat | tagagctaaa | gaataataat | ttaactccag | ttgagaaaaa | tttacatttt | 300 |
| gttgcgattg | gaggtcaaat | aaatgacact | gctattaatt | atataaatca | atggaaagat | 360 |
| gtaaatagtg | attataatgt | taatgttttt | tatgatagta | atgcattttt | gataaacaca | 420 |
| ttgaaaaaaa | ctgtagtaga | atcagcaata | aatgatacac | ttgaatcatt | tagagaaaac | 480 |
| ttaaatgacc | ctagatttga | ctataataaa | ttcttcagaa | aacgtatgga | aataatttat | 540 |
| gataaacaga | aaaatttcat | aaactactat | aaagctcaaa | gagaagaaaa | tcctgaactt | 600 |
| ataattgatg | atattgtaaa | gacatatctt | tcaaatgagt | attcaaagga | gatagatgaa | 660 |
| cttaatacct | atattgaaga | atccttaaat | aaaattacac | agaatagtgg | aaatgatgtt | 720 |
| agaaactttg | aagaatttaa | aaatggagag | tcattcaact | tatatgaaca | agagttggta | 780 |
| gaaaggtgga | atttagctgc | tgcttctgac | atattaagaa | tatctgcatt | aaaagaaatt | 840 |
| ggtggtatgt | atttagatgt | taatatgtta | ccaggaatac | aaccagactt | atttgagtct | 900 |
| atagagaaac | ctagttcagt | aacagtggat | ttttgggaaa | tgacaaagtt | agaagctata | 960 |
| atgaaataca | agaatatat | accagaatat | acctcagaac | attttgacat | gttagacgaa | 1020 |
| gaagttcaaa | gtagttttga | atctgttcta | gcttctaagt | cagataaatc | agaaatattc | 1080 |
| tcatcacttg | gtgatatgga | ggcatcacca | ctagaagtta | aaattgcatt | taatagtaag | 1140 |
| ggtattataa | atcaagggct | aatttctgtg | aaagactcat | attgtagcaa | tttaatagta | 1200 |
| aaacaaatcg | agaatagata | taaaatattg | aataatagtt | taaatccagc | tattagcgag | 1260 |
| gataatgatt | ttaatactac | aacgaatacc | tttattgata | gtataatggc | tgaagctaat | 1320 |
| gcagataatg | gtagatttat | gatggaacta | ggaaagtatt | taagagttgg | tttcttccca | 1380 |
| gatgttaaaa | ctactattaa | cttaagtggc | cctgaagcat | atgcggcagc | ttatcaagat | 1440 |
| ttattaatgt | ttaaagaagg | cagtatgaat | atccatttga | tagaagctga | tttaagaaac | 1500 |
| tttgaaatct | ctaaaactaa | tatttctcaa | tcaactgaac | aagaaatggc | tagcttatgg | 1560 |
| tcatttgacg | atgcaagagc | taaagctcaa | tttgaagaat | ataaaggaa | ttattttgaa | 1620 |
| ggttctcttg | gtgaagatga | taatcttgat | ttttctcaaa | atatagtagt | tgacaaggag | 1680 |
| tatcttttag | aaaaaatatc | ttcattagca | agaagttcag | agagaggata | tatacactat | 1740 |
| attgttcagt | acaaggagaa | taaattagt | tatgaagcag | catgtaactt | atttgcaaag | 1800 |
| actccttatg | atagtgtact | gtttcagaaa | aatatagaag | attcagaaat | tgcatattat | 1860 |
| tataatcctg | gagatggtga | aatacaagaa | atagacaagt | ataaaattcc | aagtataatt | 1920 |
| tctgatagac | ctaagattaa | attaacattt | attggtcatg | gtaaagatga | atttaatact | 1980 |
| gatatatttg | caggttttga | tgtagattca | ttatccacag | aaatagaagc | agcaatagat | 2040 |
| ttagctaaag | aggatatttc | tcctaagtca | atagaaataa | atttattagg | atgtaatatg | 2100 |
| tttagctact | ctatcaacgt | agaggagact | tatcctggaa | aattattact | taaagttaaa | 2160 |

```
gataaaatat cagaattaat gccatctata agtcaagact ctattatagt aagtgcaaat    2220
caatatgaag ttagaataaa tagtgaagga agaagagaat tattggatca ttctggtgaa    2280
tggataaata agaagaaag tggtggctct ggtataactg gatttgtgac tgtaggcgat    2340
gataaatact actttaatcc aattaatggt ggagctgctt caattggaga gacaataatt    2400
gatgacaaaa attattattt caaccaaagt ggagtgttac aaacaggtgt atttagtaca    2460
gaagatggat ttaaatattt tgccccagct aatacacttg atgaaaacct agaaggagaa    2520
gcaattgatt ttactggaaa attaattatt gacgaaaata tttattattt tgatgataat    2580
tatagaggag ctgtagaatg gaaagaatta gatggtgaaa tgcactattt tagcccagaa    2640
acaggtaaag cttttaaagg tctaaatcaa ataggtgatt ataaatacta tttcaattct    2700
gatggagtta tgcaaaaagg atttgttagt ataaatgata taaacacta ttttgatgat    2760 tctggtgtta tgaaagtagg ttacactgaa atagatggca agcatttcta ctttgctgaa    2820
aacggagaaa tgcaaatagg agtatttaat acagaagatg gatttaaata ttttgctcat    2880
cataatgaag atttaggaaa tgaagaaggt gaagaaatct caggtggctc tggtaaaatg    2940
gtaacaggag tatttaaagg acctaatgga tttgagtatt ttgcacctgc taatactcac    3000
aataataaca tagaaggtca ggctatagtt taccagaaca aattcttaac tttgaatggc    3060
aaaaaatatt attttgataa tgactcaaaa gcagttactg atggcaaac cattgatggt    3120 aaaaaatatt actttaatct taacactgct gaagcagcta ctggatggca aactattgat    3180
ggtaaaaaat attacttta tcttaacact gctgaagcag ctactggatg caaactatt    3240 gatggtaaaa aatattactt taatactaac actttcatag cctcaactgg ttatacaagt    3300
attaatggta acatttttta ttttaatact gatggtatta tgcagatagg agtgtttaaa    3360
ggacctaatg gatttgaata ctttgcacct gctaatacgg atgctaacaa catagaaggt    3420
caagctatac tttaccaaaa taaattctta actttgaatg gtaaaaaata ttactttggt    3480
agtgactcaa aagcagttac cggactgcga actattgatg gtaaaaaata ttactttaat    3540
actaacactg ctgttgcagt tactggatgg caaactatta tggtaaaaaa atactacttt    3600
aatactaaca cttctatagc ttcaactggt tatacaatta ttagtggtaa acattttat    3660 tttaatactg atggtattat gcagatagga gtgtttaaag gacctgatgg atttgaatac    3720
tttgcacctg ctaatacaga tgctaacaat atagaaggtc aagctatacg ttatcaaaat    3780
agattcctat atttacatga caatatatat tattttggta ataattcaaa agcggctact    3840
ggttgggtaa ctattgatgg taatagatat tacttcgagc ctaatacagc tatgggtgcg    3900
aatggttata aaactattga taataaaaat ttttacttta gaaatggttt acctcagata    3960
ggagtgttta agggtctaa tggatttgaa actttgcac ctgctaatac ggatgctaac    4020
aatatagaag gtcaagctat acgttatcaa aatagattcc tacatttact tggaaaaata    4080
tattactttg gtaataattc aaaagcagtt actggatggc aaactattaa tggtaaagta    4140
tattacttta tgcctgatac tgctatggct gcagctggtg acttttcga gattgatggt    4200 gttatatatt ctttggtgt tgatggagta aaagcccctg ggatatatgg g             4251
```

<210> SEQ ID NO 3
<211> LENGTH: 1417
<212> TYPE: PRT
<213> ORGANISM: Artificial Sequence
<220> FEATURE:
<223> OTHER INFORMATION: Synthetic

<400> SEQUENCE: 3

-continued

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
            130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
                180                 185                 190

Gln Arg Glu Glu Asn Pro Glu Leu Ile Ile Asp Asp Ile Val Lys Thr
            195                 200                 205

Tyr Leu Ser Asn Glu Tyr Ser Lys Glu Ile Asp Glu Leu Asn Thr Tyr
210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asn
            275                 280                 285

Met Leu Pro Gly Ile Gln Pro Asp Leu Phe Glu Ser Ile Glu Lys Pro
            290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
            355                 360                 365

Ser Pro Leu Glu Val Lys Ile Ala Phe Asn Ser Lys Gly Ile Ile Asn
            370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415
```

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
            450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
            485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
            530                 535                 540

Glu Asp Asp Asn Leu Asp Phe Ser Gln Asn Ile Val Val Asp Lys Glu
545                 550                 555                 560

Tyr Leu Glu Lys Ile Ser Ser Leu Ala Arg Ser Ser Glu Arg Gly
            565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Asn Pro Gly
            610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
            645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Ala Asn Met Phe Ser Tyr Ser
            690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
            725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Gly
            755                 760                 765

Gly Ser Gly Ile Thr Gly Phe Val Thr Val Gly Asp Asp Lys Tyr Tyr
            770                 775                 780

Phe Asn Pro Ile Asn Gly Gly Ala Ala Ser Ile Gly Glu Thr Ile Ile
785                 790                 795                 800

Asp Asp Lys Asn Tyr Tyr Phe Asn Gln Ser Gly Val Leu Gln Thr Gly
            805                 810                 815

Val Phe Ser Thr Glu Asp Gly Phe Lys Tyr Phe Ala Pro Ala Asn Thr
            820                 825                 830

Leu Asp Glu Asn Leu Glu Gly Glu Ala Ile Asp Phe Thr Gly Lys Leu

```
                835                 840                 845
Ile Ile Asp Glu Asn Ile Tyr Tyr Phe Asp Asp Asn Tyr Arg Gly Ala
        850                 855                 860
Val Glu Trp Lys Glu Leu Asp Gly Glu Met His Tyr Phe Ser Pro Glu
865                 870                 875                 880
Thr Gly Lys Ala Phe Lys Gly Leu Asn Gln Ile Gly Asp Tyr Lys Tyr
                885                 890                 895
Tyr Phe Asn Ser Asp Gly Val Met Gln Lys Gly Phe Val Ser Ile Asn
        900                 905                 910
Asp Asn Lys His Tyr Phe Asp Asp Ser Gly Val Met Lys Val Gly Tyr
                915                 920                 925
Thr Glu Ile Asp Gly Lys His Phe Tyr Phe Ala Glu Asn Gly Glu Met
        930                 935                 940
Gln Ile Gly Val Phe Asn Thr Glu Asp Gly Phe Lys Tyr Phe Ala His
945                 950                 955                 960
His Asn Glu Asp Leu Gly Asn Glu Glu Gly Glu Glu Ile Ser Gly Gly
                965                 970                 975
Ser Gly Lys Met Val Thr Gly Val Phe Lys Gly Pro Asn Gly Phe Glu
                980                 985                 990
Tyr Phe Ala Pro Ala Asn Thr His  Asn Asn Asn Ile Glu  Gly Gln Ala
                995                 1000                1005
Ile Val  Tyr Gln Asn Lys Phe  Leu Thr Leu Asn Gly  Lys Lys Tyr
    1010                1015                1020
Tyr Phe  Asp Asn Asp Ser Lys  Ala Val Thr Gly Trp  Gln Thr Ile
    1025                1030                1035
Asp Gly  Lys Lys Tyr Tyr Phe  Asn Leu Asn Thr Ala  Glu Ala Ala
    1040                1045                1050
Thr Gly  Trp Gln Thr Ile Asp  Gly Lys Lys Tyr Tyr  Phe Asn Leu
    1055                1060                1065
Asn Thr  Ala Glu Ala Ala Thr  Gly Trp Gln Thr Ile  Asp Gly Lys
    1070                1075                1080
Lys Tyr  Tyr Phe Asn Thr Asn  Thr Phe Ile Ala Ser  Thr Gly Tyr
    1085                1090                1095
Thr Ser  Ile Asn Gly Lys His  Phe Tyr Phe Asn Thr  Asp Gly Ile
    1100                1105                1110
Met Gln  Ile Gly Val Phe Lys  Gly Pro Asn Gly Phe  Glu Tyr Phe
    1115                1120                1125
Ala Pro  Ala Asn Thr Asp Ala  Asn Asn Ile Glu Gly  Gln Ala Ile
    1130                1135                1140
Leu Tyr  Gln Asn Lys Phe Leu  Thr Leu Asn Gly Lys  Lys Tyr Tyr
    1145                1150                1155
Phe Gly  Ser Asp Ser Lys Ala  Val Thr Gly Leu Arg  Thr Ile Asp
    1160                1165                1170
Gly Lys  Lys Tyr Tyr Phe Asn  Thr Asn Thr Ala Val  Ala Val Thr
    1175                1180                1185
Gly Trp  Gln Thr Ile Asn Gly  Lys Lys Tyr Tyr Phe  Asn Thr Asn
    1190                1195                1200
Thr Ser  Ile Ala Ser Thr Gly  Tyr Thr Ile Ile Ser  Gly Lys His
    1205                1210                1215
Phe Tyr  Phe Asn Thr Asp Gly  Ile Met Gln Ile Gly  Val Phe Lys
    1220                1225                1230
Gly Pro  Asp Gly Phe Glu Tyr  Phe Ala Pro Ala Asn  Thr Asp Ala
    1235                1240                1245
```

Asn Asn Ile Glu Gly Gln Ala Ile Arg Tyr Gln Asn Arg Phe Leu
    1250                1255                1260

Tyr Leu His Asp Asn Ile Tyr Tyr Phe Gly Asn Asn Ser Lys Ala
    1265                1270                1275

Ala Thr Gly Trp Val Thr Ile Asp Gly Asn Arg Tyr Tyr Phe Glu
    1280                1285                1290

Pro Asn Thr Ala Met Gly Ala Asn Gly Tyr Lys Thr Ile Asp Asn
    1295                1300                1305

Lys Asn Phe Tyr Phe Arg Asn Gly Leu Pro Gln Ile Gly Val Phe
    1310                1315                1320

Lys Gly Ser Asn Gly Phe Glu Tyr Phe Ala Pro Ala Asn Thr Asp
    1325                1330                1335

Ala Asn Asn Ile Glu Gly Gln Ala Ile Arg Tyr Gln Asn Arg Phe
    1340                1345                1350

Leu His Leu Leu Gly Lys Ile Tyr Tyr Phe Gly Asn Asn Ser Lys
    1355                1360                1365

Ala Val Thr Gly Trp Gln Thr Ile Asn Gly Lys Val Tyr Tyr Phe
    1370                1375                1380

Met Pro Asp Thr Ala Met Ala Ala Ala Gly Gly Leu Phe Glu Ile
    1385                1390                1395

Asp Gly Val Ile Tyr Phe Phe Gly Val Asp Gly Val Lys Ala Pro
    1400                1405                1410

Gly Ile Tyr Gly
    1415

<210> SEQ ID NO 4
<211> LENGTH: 1210
<212> TYPE: PRT
<213> ORGANISM: Artificial Sequence
<220> FEATURE:
<223> OTHER INFORMATION: Synthetic

<400> SEQUENCE: 4

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

-continued

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asn
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

-continued

Ala Ala Cys Asn Leu Phe Ala Lys Thr Pro Tyr Asp Ser Val Leu Phe
           595                 600                 605

Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Gly
        755                 760                 765

Gly Ser Gly Lys Met Val Thr Gly Val Phe Lys Gly Pro Asn Gly Phe
    770                 775                 780

Glu Tyr Phe Ala Pro Ala Asn Thr His Asn Asn Asn Ile Glu Gly Gln
785                 790                 795                 800

Ala Ile Val Tyr Gln Asn Lys Phe Leu Thr Leu Asn Gly Lys Lys Tyr
                805                 810                 815

Tyr Phe Asp Asn Asp Ser Lys Ala Val Thr Gly Trp Gln Thr Ile Asp
            820                 825                 830

Gly Lys Lys Tyr Tyr Phe Asn Leu Asn Thr Ala Glu Ala Ala Thr Gly
        835                 840                 845

Trp Gln Thr Ile Asp Gly Lys Lys Tyr Tyr Phe Asn Leu Asn Thr Ala
    850                 855                 860

Glu Ala Ala Thr Gly Trp Gln Thr Ile Asp Gly Lys Lys Tyr Tyr Phe
865                 870                 875                 880

Asn Thr Asn Thr Phe Ile Ala Ser Thr Gly Tyr Thr Ser Ile Asn Gly
                885                 890                 895

Lys His Phe Tyr Phe Asn Thr Asp Gly Ile Met Gln Ile Gly Val Phe
            900                 905                 910

Lys Gly Pro Asn Gly Phe Glu Tyr Phe Ala Pro Ala Asn Thr Asp Ala
        915                 920                 925

Asn Asn Ile Glu Gly Gln Ala Ile Leu Tyr Gln Asn Lys Phe Leu Thr
    930                 935                 940

Leu Asn Gly Lys Lys Tyr Tyr Phe Gly Ser Asp Ser Lys Ala Val Thr
945                 950                 955                 960

Gly Leu Arg Thr Ile Asp Gly Lys Lys Tyr Tyr Phe Asn Thr Asn Thr
                965                 970                 975

Ala Val Ala Val Thr Gly Trp Gln Thr Ile Asn Gly Lys Lys Tyr Tyr
            980                 985                 990

Phe Asn Thr Asn Thr Ser Ile Ala Ser Thr Gly Tyr Thr Ile Ile Ser
        995                 1000                 1005

Gly Lys His Phe Tyr Phe Asn Thr Asp Gly Ile Met Gln Ile Gly

```
            1010                1015                1020

Val Phe Lys Gly Pro Asp Gly Phe Glu Tyr Phe Ala Pro Ala Asn
            1025                1030                1035

Thr Asp Ala Asn Asn Ile Glu Gly Gln Ala Ile Arg Tyr Gln Asn
            1040                1045                1050

Arg Phe Leu Tyr Leu His Asp Asn Ile Tyr Tyr Phe Gly Asn Asn
            1055                1060                1065

Ser Lys Ala Ala Thr Gly Trp Val Thr Ile Asp Gly Asn Arg Tyr
            1070                1075                1080

Tyr Phe Glu Pro Asn Thr Ala Met Gly Ala Asn Gly Tyr Lys Thr
            1085                1090                1095

Ile Asp Asn Lys Asn Phe Tyr Phe Arg Asn Gly Leu Pro Gln Ile
            1100                1105                1110

Gly Val Phe Lys Gly Ser Asn Gly Phe Glu Tyr Phe Ala Pro Ala
            1115                1120                1125

Asn Thr Asp Ala Asn Asn Ile Glu Gly Gln Ala Ile Arg Tyr Gln
            1130                1135                1140

Asn Arg Phe Leu His Leu Leu Gly Lys Ile Tyr Tyr Phe Gly Asn
            1145                1150                1155

Asn Ser Lys Ala Val Thr Gly Trp Gln Thr Ile Asn Gly Lys Val
            1160                1165                1170

Tyr Tyr Phe Met Pro Asp Thr Ala Met Ala Ala Ala Gly Gly Leu
            1175                1180                1185

Phe Glu Ile Asp Gly Val Ile Tyr Phe Phe Gly Val Asp Gly Val
            1190                1195                1200

Lys Ala Pro Gly Ile Tyr Gly
            1205                1210

<210> SEQ ID NO 5
<211> LENGTH: 767
<212> TYPE: PRT
<213> ORGANISM: Artificial Sequence
<220> FEATURE:
<223> OTHER INFORMATION: Synthetic

<400> SEQUENCE: 5

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
```

-continued

```
            145                 150                 155                 160

Leu Asn Asp Pro Arg Phe Asp Tyr Asn Lys Phe Phe Arg Lys Arg Met
                    165                 170                 175

Glu Ile Ile Tyr Asp Lys Gln Lys Asn Phe Ile Asn Tyr Tyr Lys Ala
                    180                 185                 190

Gln Arg Glu Glu Asn Pro Glu Leu Ile Ile Asp Asp Ile Val Lys Thr
                    195                 200                 205

Tyr Leu Ser Asn Glu Tyr Ser Lys Glu Ile Asp Glu Leu Asn Thr Tyr
        210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                    245                 250                 255

Gln Glu Leu Val Glu Arg Trp Asn Leu Ala Ala Ala Ser Asp Ile Leu
                    260                 265                 270

Arg Ile Ser Ala Leu Lys Glu Ile Gly Gly Met Tyr Leu Asp Val Asn
                    275                 280                 285

Met Leu Pro Gly Ile Gln Pro Asp Leu Phe Glu Ser Ile Glu Lys Pro
        290                 295                 300

Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                    325                 330                 335

Met Leu Asp Glu Glu Val Gln Ser Ser Phe Glu Ser Val Leu Ala Ser
                    340                 345                 350

Lys Ser Asp Lys Ser Glu Ile Phe Ser Ser Leu Gly Asp Met Glu Ala
                    355                 360                 365

Ser Pro Leu Glu Val Lys Ile Ala Phe Asn Ser Lys Gly Ile Ile Asn
        370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                    405                 410                 415

Ala Ile Ser Glu Asp Asn Asp Phe Asn Thr Thr Asn Thr Phe Ile
                    420                 425                 430

Asp Ser Ile Met Ala Glu Ala Asn Ala Asp Asn Gly Arg Phe Met Met
                    435                 440                 445

Glu Leu Gly Lys Tyr Leu Arg Val Gly Phe Phe Pro Asp Val Lys Thr
        450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                    485                 490                 495

Asp Leu Arg Asn Phe Glu Ile Ser Lys Thr Asn Ile Ser Gln Ser Thr
                    500                 505                 510

Glu Gln Glu Met Ala Ser Leu Trp Ser Phe Asp Asp Ala Arg Ala Lys
                    515                 520                 525

Ala Gln Phe Glu Glu Tyr Lys Arg Asn Tyr Phe Glu Gly Ser Leu Gly
                    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                    565                 570                 575
```

```
Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser
        755                 760                 765

<210> SEQ ID NO 6
<211> LENGTH: 439
<212> TYPE: PRT
<213> ORGANISM: Artificial Sequence
<220> FEATURE:
<223> OTHER INFORMATION: Synthetic

<400> SEQUENCE: 6

Lys Met Val Thr Gly Val Phe Lys Gly Pro Asn Gly Phe Glu Tyr Phe
1               5                   10                  15

Ala Pro Ala Asn Thr His Asn Asn Ile Glu Gly Gln Ala Ile Val
            20                  25                  30

Tyr Gln Asn Lys Phe Leu Thr Leu Asn Gly Lys Lys Tyr Tyr Phe Asp
        35                  40                  45

Asn Asp Ser Lys Ala Val Thr Gly Trp Gln Thr Ile Asp Gly Lys Lys
50                  55                  60

Tyr Tyr Phe Asn Leu Asn Thr Ala Glu Ala Thr Gly Trp Gln Thr
65                  70                  75                  80

Ile Asp Gly Lys Lys Tyr Tyr Phe Asn Leu Asn Thr Ala Glu Ala Ala
                85                  90                  95

Thr Gly Trp Gln Thr Ile Asp Gly Lys Lys Tyr Tyr Phe Asn Thr Asn
            100                 105                 110

Thr Phe Ile Ala Ser Thr Gly Tyr Thr Ser Ile Asn Gly Lys His Phe
        115                 120                 125

Tyr Phe Asn Thr Asp Gly Ile Met Gln Ile Gly Val Phe Lys Gly Pro
    130                 135                 140

Asn Gly Phe Glu Tyr Phe Ala Pro Ala Asn Thr Asp Ala Asn Asn Ile
145                 150                 155                 160

Glu Gly Gln Ala Ile Leu Tyr Gln Asn Lys Phe Leu Thr Leu Asn Gly
                165                 170                 175
```

Lys Lys Tyr Tyr Phe Gly Ser Asp Ser Lys Ala Val Thr Gly Leu Arg
            180                 185                 190

Thr Ile Asp Gly Lys Lys Tyr Tyr Phe Asn Thr Asn Thr Ala Val Ala
        195                 200                 205

Val Thr Gly Trp Gln Thr Ile Asn Gly Lys Lys Tyr Tyr Phe Asn Thr
210                 215                 220

Asn Thr Ser Ile Ala Ser Thr Gly Tyr Thr Ile Ile Ser Gly Lys His
225                 230                 235                 240

Phe Tyr Phe Asn Thr Asp Gly Ile Met Gln Ile Gly Val Phe Lys Gly
                245                 250                 255

Pro Asp Gly Phe Glu Tyr Phe Ala Pro Ala Asn Thr Asp Ala Asn Asn
            260                 265                 270

Ile Glu Gly Gln Ala Ile Arg Tyr Gln Asn Arg Phe Leu Tyr Leu His
        275                 280                 285

Asp Asn Ile Tyr Tyr Phe Gly Asn Asn Ser Lys Ala Ala Thr Gly Trp
290                 295                 300

Val Thr Ile Asp Gly Asn Arg Tyr Tyr Phe Glu Pro Asn Thr Ala Met
305                 310                 315                 320

Gly Ala Asn Gly Tyr Lys Thr Ile Asp Asn Lys Asn Phe Tyr Phe Arg
                325                 330                 335

Asn Gly Leu Pro Gln Ile Gly Val Phe Lys Gly Ser Asn Gly Phe Glu
            340                 345                 350

Tyr Phe Ala Pro Ala Asn Thr Asp Ala Asn Asn Ile Glu Gly Gln Ala
        355                 360                 365

Ile Arg Tyr Gln Asn Arg Phe Leu His Leu Leu Gly Lys Ile Tyr Tyr
370                 375                 380

Phe Gly Asn Asn Ser Lys Ala Val Thr Gly Trp Gln Thr Ile Asn Gly
385                 390                 395                 400

Lys Val Tyr Tyr Phe Met Pro Asp Thr Ala Met Ala Ala Ala Gly Gly
                405                 410                 415

Leu Phe Glu Ile Asp Gly Val Ile Tyr Phe Phe Gly Val Asp Gly Val
            420                 425                 430

Lys Ala Pro Gly Ile Tyr Gly
            435

<210> SEQ ID NO 7
<211> LENGTH: 203
<212> TYPE: PRT
<213> ORGANISM: Artificial Sequence
<220> FEATURE:
<223> OTHER INFORMATION: Synthetic

<400> SEQUENCE: 7

Ile Thr Gly Phe Val Thr Val Gly Asp Asp Lys Tyr Tyr Phe Asn Pro
1               5                   10                  15

Ile Asn Gly Gly Ala Ala Ser Ile Gly Glu Thr Ile Ile Asp Asp Lys
            20                  25                  30

Asn Tyr Tyr Phe Asn Gln Ser Gly Val Leu Gln Thr Gly Val Phe Ser
        35                  40                  45

Thr Glu Asp Gly Phe Lys Tyr Phe Ala Pro Ala Asn Thr Leu Asp Glu
    50                  55                  60

Asn Leu Glu Gly Glu Ala Ile Asp Phe Thr Gly Lys Leu Ile Ile Asp
65                  70                  75                  80

Glu Asn Ile Tyr Tyr Phe Asp Asp Asn Tyr Arg Gly Ala Val Glu Trp
                85                  90                  95

```
Lys Glu Leu Asp Gly Glu Met His Tyr Phe Ser Pro Glu Thr Gly Lys
            100                 105                 110

Ala Phe Lys Gly Leu Asn Gln Ile Gly Asp Tyr Lys Tyr Tyr Phe Asn
            115                 120                 125

Ser Asp Gly Val Met Gln Lys Gly Phe Val Ser Ile Asn Asp Asn Lys
    130             135                 140

His Tyr Phe Asp Asp Ser Gly Val Met Lys Val Gly Tyr Thr Glu Ile
145             150                 155                 160

Asp Gly Lys His Phe Tyr Phe Ala Glu Asn Gly Glu Met Gln Ile Gly
                165             170                 175

Val Phe Asn Thr Glu Asp Gly Phe Lys Tyr Phe Ala His His Asn Glu
            180                 185                 190

Asp Leu Gly Asn Glu Glu Gly Glu Glu Ile Ser
        195                 200
```